(12) United States Patent
Waxman et al.

(10) Patent No.: US 8,775,340 B2
(45) Date of Patent: Jul. 8, 2014

(54) DETECTION AND PREDICTION OF PHYSIOLOGICAL EVENTS IN PEOPLE WITH SLEEP DISORDERED BREATHING USING A LAMSTAR NEURAL NETWORK

(75) Inventors: Jonathan Waxman, Chicago, IL (US); Daniel Graupe, Chicago, IL (US); David W. Carley, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 244 days.

(21) Appl. No.: 13/140,580

(22) PCT Filed: Dec. 15, 2009

(86) PCT No.: PCT/US2009/068110
§ 371 (c)(1),
(2), (4) Date: Jun. 17, 2011

(87) PCT Pub. No.: WO2010/080405
PCT Pub. Date: Jul. 15, 2010

(65) Prior Publication Data
US 2011/0251985 A1    Oct. 13, 2011

Related U.S. Application Data

(60) Provisional application No. 61/106,027, filed on Dec. 19, 2008.

(51) Int. Cl.
*G06N 3/04* (2006.01)
*A61B 5/00* (2006.01)

(52) U.S. Cl.
CPC .... *G06N 3/04* (2013.01); *A61B 5/72* (2013.01)
USPC .............................................. 706/20; 706/45

(58) Field of Classification Search
CPC ................................... G06N 3/04; A61B 5/72
USPC ...................................................... 706/20, 45
See application file for complete search history.

(56) References Cited

U.S. PATENT DOCUMENTS 5,920,852 A    7/1999    Graupe
7,747,316 B2    6/2010    Graupe et al.

FOREIGN PATENT DOCUMENTS

WO    WO2005/112760    12/2005

OTHER PUBLICATIONS

Graupe, et al., A Large Scale Memory (LAMSTAR) Neural Network for Medical Diagnosis, Proceedings—19th International Conference—IEEE/EMBS Oct. 30-Nov. 2, 1997, pp. 1332-1335.*
Liu et al., A Neural Network Method for Detection of Obstructive Sleep Apnea and Narcolepsy Based on Pupil Size and EEG, IEEE Transactions on Neural Networks, vol. 19, No. 2, Feb. 2008, pp. 308-318.*
International Preliminary Report on Patentability, PCT International Application No. PCT/US2009/068110, issued Jun. 21, 2011.
International Search Report and Written Opinion, PCT International Application No. PCT/US2009/068110 dated Apr. 6, 2010.

(Continued)

*Primary Examiner* — Wilbert L Starks
(74) *Attorney, Agent, or Firm* — McDonnell Boehnen Hulbert & Berghoff LLP

(57) ABSTRACT

Apparatus and methods are disclosed for generating and outputting physiological event results from physiological data related to a patient. Physiological event results include results predicting and/or detecting individual physiological events related to a medical condition of the patient.

29 Claims, 16 Drawing Sheets

(56) References Cited

OTHER PUBLICATIONS

Khandoker, AH et al., "Recognizing Central and Obstructive Sleep Apnea Events from Normal Breathing Events in ECG Recordings", Computers in Cardiology, vol. 35, Sep. 14, 2008, pp. 681-684.

Kordylewski, Hubert al al., "A Novel Large-Memory Neural Network as an Aid in Medical Diagnosis Applications", IEEE Transactions on Information Technology in Biomedicine, vol. 5, No. 3, Sep. 2001, pp. 202-209.

Waxman, J. et al., "Automated Neural Network Detection and Prediction of Sleep Apnea", Sleep, vol. 30, Abstract Supplement, 2007, p. A353.

Waxman, Jonathan A. et al., "Automated Prediction of Apnea and Hypopnea Using a LAMSTAR Artificial Neural Network", American Journal of Respiratory and Critical Care Medicine, American Lung Association, Dec. 17, 2009, pp. 1-53.

Cvetkovic, Dean et al., "Wavelet Transform Feature Extraction from Human PPG, ECG and EEG Signal Responses to ELF PEMF Exposures: A Pilot Study", Digital Signal Processing, vol. 18, No. 5, Sep. 1, 2008, pp. 861-874.

Graupe, Daniel, "Chapter 13—Large Scale Memory Storage and Retrieval (LAMSTAR) Network", Principles of Artificial Neural Networks, World Scientific, Jan. 1, 2007, pp. 249-284.

* cited by examiner

DETECTION AND PREDICTION OF PHYSIOLOGICAL EVENTS IN PEOPLE WITH SLEEP DISORDERED BREATHING USING A LAMSTAR NEURAL NETWORK

RELATED APPLICATIONS

The present application claims priority to U.S. Provisional Patent Application No. 61/106,027 entitled "Detection and Prediction of Physiological Events in People with Sleep Disordered Breathing Using a LAMSTAR Neural Network", filed Dec. 19, 2008, which is entirely incorporated by reference herein for all purposes.

BACKGROUND OF THE INVENTION

1. Field of the Invention

This invention relates to medical devices, and more particularly, to prediction and detection of physiological events.

2. Background

Many diagnostic and therapeutic medical devices are equipped to detect physiological events. For example, a widely respected diagnostic test for sleep-related disorders, such as obstructive sleep apnea syndrome, is polysomnography, in which respiratory, cardiac, muscular, and neurological parameters are monitored during sleep by a polysomnogram.

The polysomnogram will typically record data from a number of different data sources requiring a number of wire attachments to the patient—often more than 20 different wires are used. These data sources typically include:
- one or more electroencephalogram (EEG) channels to monitor brain activity,
- one or more pressure transducers, thermocouples, and/or thermistors, fitted in or near the nostrils, for monitoring nasal airflow and/or temperature,
- one or more microphones to monitor breathing sounds, including snoring,
- one or more electromyogram (EMG) channels for measuring chin and/or leg movements,
- one or more electrooculogram (EOG) channels to monitor eye movements,
- one or more electrocardiogram (EKG) channels for detecting heart rate and rhythm, including heart rate variability (HRV),
- a pulse oximeter to measure oxygen saturation of arterial hemoglobin, and/or
- belts placed around the patient to measure chest wall and abdominal wall movement.

In conjunction with assessment of daytime symptoms, using a polysomnogram to measure the frequency of sleep-related apnea (cessation of breathing) and/or hypopnea (marked reduction in tidal volume) represents the standard of care for diagnosing obstructive sleep apnea (OSA) syndrome.

Obstructive sleep apnea syndrome is the most common sleep-related breathing disorder, with a prevalence of at least 4% in men and 2% in women aged 20 to 60 years, and thus is a major public health problem with a societal impact comparable to that of smoking Studies have revealed associations with cardiovascular disease, stroke, and diabetes and people with obstructive sleep apnea syndrome commonly experience excessive daytime sleepiness and cognitive dysfunction, placing them at risk for motor vehicle accidents and work related injuries.

The most common therapy for obstructive sleep apnea syndrome is continuous positive airway pressure (CPAP), which attempts to overcome mechanical collapsing forces in the airways by continuously blowing air into the nose. Although largely effective, for many CPAP is cumbersome and difficult to tolerate, resulting in poor long-term compliance. To reduce pressure exposure, auto-adjusting positive airway pressure (APAP) devices are used in some cases. APAP devices typically rely on early detection of respiratory events to make pressure adjustments.

These conventional therapies for obstructive sleep apnea syndrome are largely effective but suffer from poor patient compliance. In some patients, the conventional therapies do not fully alleviate all adverse consequences, including obstructive-sleep-apnea-associated cardiovascular risk factors, daytime sleepiness, and decreased quality of life. Methods and devices capable of detecting and predicting individual physiological events, such as apneas and hypopneas, are needed to provide improved treatment, compliance, and effectiveness of these conventional therapies.

SUMMARY

This application provides methods and instruments capable of detecting and predicting individual physiological events, such as apneas and hypopneas, and methods for providing improved treatment, compliance, and effectiveness of these conventional therapies directed towards sleep-related disorders.

In one aspect of the application, methods are provided. Physiological data related to a patient are received at a physiological event processor, and the data gathered from an input data source of one or more input data sources. The physiological data are segmented at the physiological event processor into a plurality of segments. The plurality of segments represent a predetermined duration of data. The data are gathered from an input data source of the one or more input data sources. At the physiological event processor, the plurality of segments are transformed into a plurality of transformed segments by using at least one transformation on the plurality of segments. An exemplary transformation is a wavelet transformation applied to each segment of the plurality of segments. A physiological event result based on the plurality of transformed segments is generated at the physiological event processor. The physiological event result includes information relating to a physiological event. The physiological event result also includes a significance value for at least one significant input data source of the one or more input data sources. The physiological event result is output from the physiological event processor to an output device.

In another aspect of the application, one or more apparatus are provided. The one or more apparatus includes a processing unit, a source data interface configured to communicate with one or more input data sources, an output interface, data storage, and machine-language instructions. The machine-language instructions are stored at least in the data storage. Upon execution by the processing unit, the machine-language instructions cause the processing unit to perform functions. The functions include: (a) receiving physiological data related to a patient via the source data interface, (b) segmenting the physiological data into a plurality of segments, where one or more segments of the plurality of segments represents a predetermined duration of data gathered from one or more input data sources, (c) transforming the plurality of segments into a plurality of transformed segments by using at least one transformation on the plurality of segments, (d) generating a physiological event result based on the plurality of transformed segments, where the physiological event result includes a significance value of at least one significant input data source of the one or more input data sources, and (e) outputting the physiological event result via the output interface.

In yet another aspect of the application, a tangible computer-readable medium is provided. The tangible computer-readable medium has instructions stored thereon. Upon execution by a computing device, the instructions cause the computing device to perform functions. The functions include: (a) receiving, at the computing device, physiological data related to a patient via one or more input data sources, (b) segmenting, at the computing device, the physiological data into a plurality of segments, where one or more segments of the plurality of segments represent a predetermined duration of data gathered from one or more input data sources, (c) transforming, at the computing device, the plurality of segments into a plurality of transformed segments by using at least one transformation on the plurality of segments, (d) generating, at the computing device, a physiological event result based on the plurality of transformed segments, where the physiological event result includes information related to a physiological event and also includes a significance value for a significant input data source of the one or more input data sources, and (e) outputting the physiological event result from the computing device.

One advantage of this application is that the physiological event processor can predict and/or detect individual physiological events, such as specific episodes of onset sleep apnea for a particular patient. A related advantage is a neural network of the physiological event processor can be effectively trained to recognize patterns in training data sequences related to physiological events. Once trained, the neural network can advantageously receive patient-related input data and accurately predict and/or detect individual physiological events for a patient. Yet another advantage of this application is that the physiological event processor, configured with an appropriately trained neural network, can enable a number of treatment and diagnostic applications.

BRIEF DESCRIPTION OF THE DRAWINGS

Various examples of particular embodiments are described herein with reference to the following drawings, wherein like numerals denote like entities, in which.

DETAILED DESCRIPTION

Figure 1:
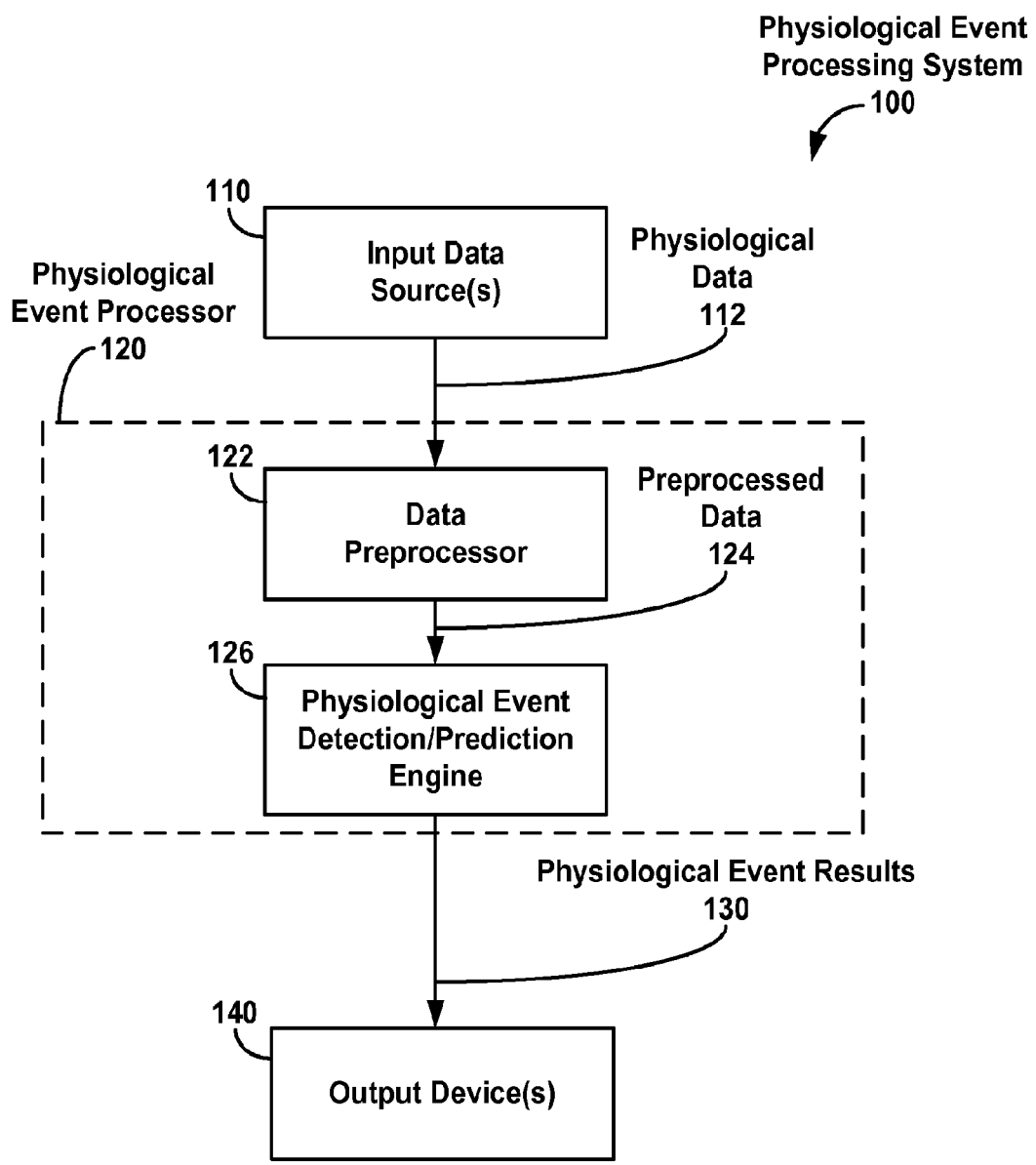
FIG. 1 is a block diagram of an exemplary physiological event processing system.

Methods and apparatus are described for detecting and predicting physiological events based on physiological data related to a patient using a physiological event processor. A physiological event is an episode related to a condition of a patient. For example, if a patient is suffering from a heart-related condition, a heart attack is a physiological event related to the heart-related condition. In another example, if a patient is suffering from a sleep-related condition, an episode of onset sleep apnea is a physiological event related to the sleep-related condition.

Physiological data includes any data related to the patient. In particular embodiments, the physiological data are gathered from a number of sources, such as medical devices (e.g., polysomnograms, electrocardiograms (EKGs), electroencephalograms (EEGs), heart rate monitors, magnetic resonance imaging (MRI) devices, X-ray machines, thermometers and other temperature measuring devices, blood pressure or blood flow measuring devices, other pressure-detecting devices, volume measuring devices, blood chemistry devices, pressure transducers, thermocouples, thermistors, electromyograms, electrooculograms, pulse oximeters, other oxygen and/or other gas sensors, movement sensors, scales, devices configured to provide data related to a patient, diagnostic devices, medical devices, and/or other devices) and/or patient input devices (e.g., mobile and/or stationary computers). In particular embodiments, the physiological data includes data related to physiological parameters, such as, but not limited to, body temperature, EKG activity (e.g., heart rate, heart rhythm, heart rate variability), EEG activity, galvanic skin response (GSR), movement rates, breathing data (e.g., nasal pressure, nasal temperature, breathing rates, tidal volume), oxygen saturation, blood chemistry parameters, drug dosages, blood pressure, blood flow, and height/weight of a patient. Physiological data are generated locally and/or remotely. If physiological data are generated remotely, the physiological data are received at the physiological event processor via one or more networks in some embodiments.

In particular embodiments, the physiological event processor includes a data preprocessor and a physiological event detection/prediction engine. The data preprocessor prepares the physiological data for use by the physiological detection/prediction engine, which then generates physiological event results based on the preprocessed physiological data. An exemplary physiological detection/prediction engine includes computer hardware and/or software configured to detect patterns in the preprocessed physiological data, such as an artificial neural network (or neural network for short). A neural network is computer hardware and/or software that, through a supervised training procedure, learns to map input patterns to desired outputs. One such neural network, described in detail below, is an appropriately trained LArge Memory STorage And Retrieval (LAMSTAR) neural network.

Physiological event results include informative and directive physiological event results. Informative physiological event results are data or other information about a physiological event, such as data predicting and/or detecting a physiological event. Directive physiological event results provide instructions, commands, and/or directions to various output devices, such as medical treatment and/or diagnostic devices.

The physiological event processor can be configured to predict and/or detect physiological events. The techniques for preprocessing data and training the LAMSTAR neural network are applicable to many different physiological conditions affecting one or more physiological systems of a patient.

Thus, the physiological event processor enables a number of treatment and diagnostic applications. One such application, described in detail below, is detection and prediction of physiological events related to sleep-related conditions, such as obstructive sleep apnea and hypopnea syndrome. In such an application, predictions of obstructive sleep apnea and/or hypopnea indicate an impending episode of abnormal breathing, such as a prediction of a sleep-related physiological event within the next 60 seconds. Once abnormal breathing is anticipated, the physiological event processor sends commands to one or more therapeutic devices. Exemplary commands include commands to control air pressure levels generated by a CPAP or APAP device and commands to a stimulator of an appropriate modality to provide sensory and/or motor stimuli to the patient to prevent or ameliorate an episode of abnormal breathing. Finer control of such therapeutic devices leads to better treatment of sleep-related conditions, including improvement of patient compliance and therapeutic outcomes.

Using the physiological event processor to predict physiological events complements current detection systems. For a sleep-related example, predictions made by the physiological event processor can enhance performance of the detection devices used in current generation APAP devices to reduce the frequency of abnormal breathing events in patients using such APAP devices. In addition, adjusting pressure levels less frequently and more gradually allows the average pressure exposure to decrease and is less disruptive to the sleep process, increasing patient comfort and adherence with APAP treatment. Also, prediction of physiological events enables earlier responses to more events and complete avoidance of other events.

A sleep-related physiological event processor improves alternative sleep apnea therapies, for instance, percutaneous or transcutaneous stimulation of various muscles and/or nerves. In particular embodiments, the prediction of an impending event triggers stimulation, and an estimate of the proximity to an impending event determines stimulation parameters.

An Exemplary Physiological Event Processing System

Turning to the drawings, FIG. 1 is a block diagram of an exemplary physiological event processing system (PEPS) 100 with input data source(s) 110, data preprocessor 122, physiological event detection/prediction engine 126, and output device(s) 140. As shown with a dashed line in FIG. 1, data processor 122 and physiological event detection/prediction engine 126 are configured as components of a physiological event processor 120.

In operation, input data source(s) 110 can be configured to provide physiological data 112 to data preprocessor 122. Data preprocessor 122 can be configured to generate preprocessed data 124 upon receiving physiological data 124 and provide preprocessed data 124 to physiological event detection/prediction engine 126. Physiological event detection/prediction engine 126 can be configured to generate physiological event results 130 based on preprocessed data 124.

Exemplary physiological event results 130 include, but are not limited to, informative physiological event results and directive physiological event results. In some embodiments, physiological event results 130 are both informative and directive; e.g., provide informative text, video, and/or audio concerning a physiological event with a command to output device(s) 140 to display the informative text, video, and/or audio. In some embodiments, output device(s) 140 further process physiological event results 130, such as by storing, formatting, collating, parsing, transmitting, and/or otherwise processing physiological event results 130. Examples include, but are not limited to, storing a plurality of physiological event results 130 in a database (including embodiments that involve additional processing), formatting physiological event results 130 for remote display via the Internet or other network, and/or parsing physiological event results 130 to generate commands for output device(s) 140.

In particular embodiments, physiological event results 130 include a significance value for one or more input data source(s) 110. For example, suppose physiological data 112 are derived from input data sources 1 and 2 (IDS1 and IDS2, for short). To indicate a significance value, physiological event results 130 can indicate that: IDS1 (or IDS2) was solely relied upon for physiological event results 130 and/or IDS1 provided more (or less) significant information for generating physiological event results 130. In some embodiments, the significance value includes numerical data for a significance of IDS1 and/or IDS2 in arriving at physiological event results 130. In other scenarios beyond this example, significance values can be used with more or fewer than two input data sources.

In some embodiments, the output device(s) 140 is configured to act upon physiological event results 130, such as by formatting and/or displaying part or all of physiological event results 130, by generating additional notification(s) based on physiological event results 130, and/or to treat physiological event results 130 as commands for further action. Exemplary commands include activating or deactivating output device(s) 140, to change behaviors of output device(s) 140, providing alarms or other warning indication(s), and/or outputting information regarding the commands.

For example, in the context of an adjustable positive airway pressure (APAP) output device used for treatment of sleep apnea syndrome, commands for further action can instruct the APAP output device to be activated/deactivated, to increase or decrease airflow to the patient, to alarm that an episode of sleep apnea and/or hypopnea has been predicted or detected, and/or to provide a notification of the commands provided to the APAP output device.

Figure 2A:
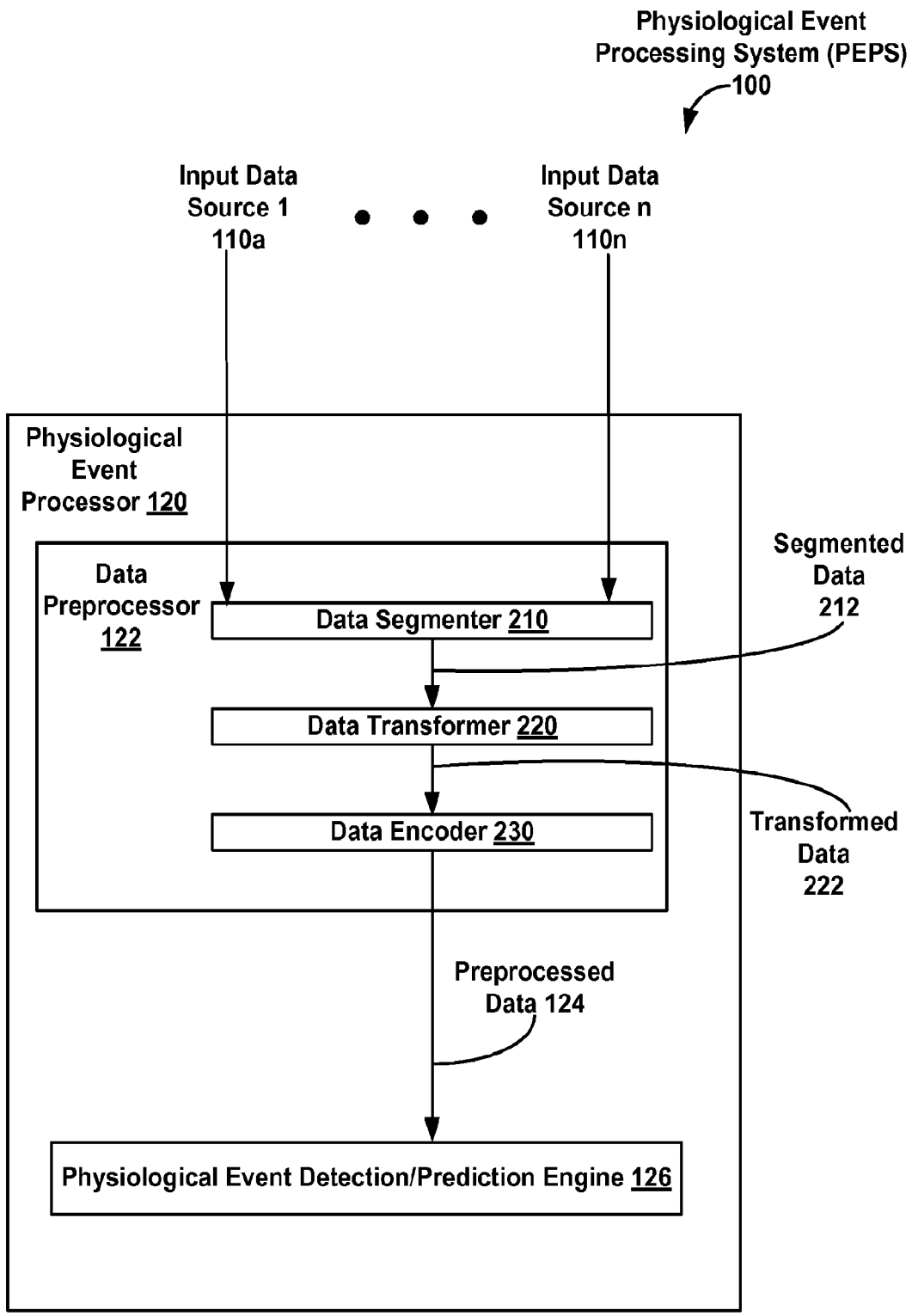
FIG. 2A is a block diagram of an exemplary data preprocessor.
Figure 2B:
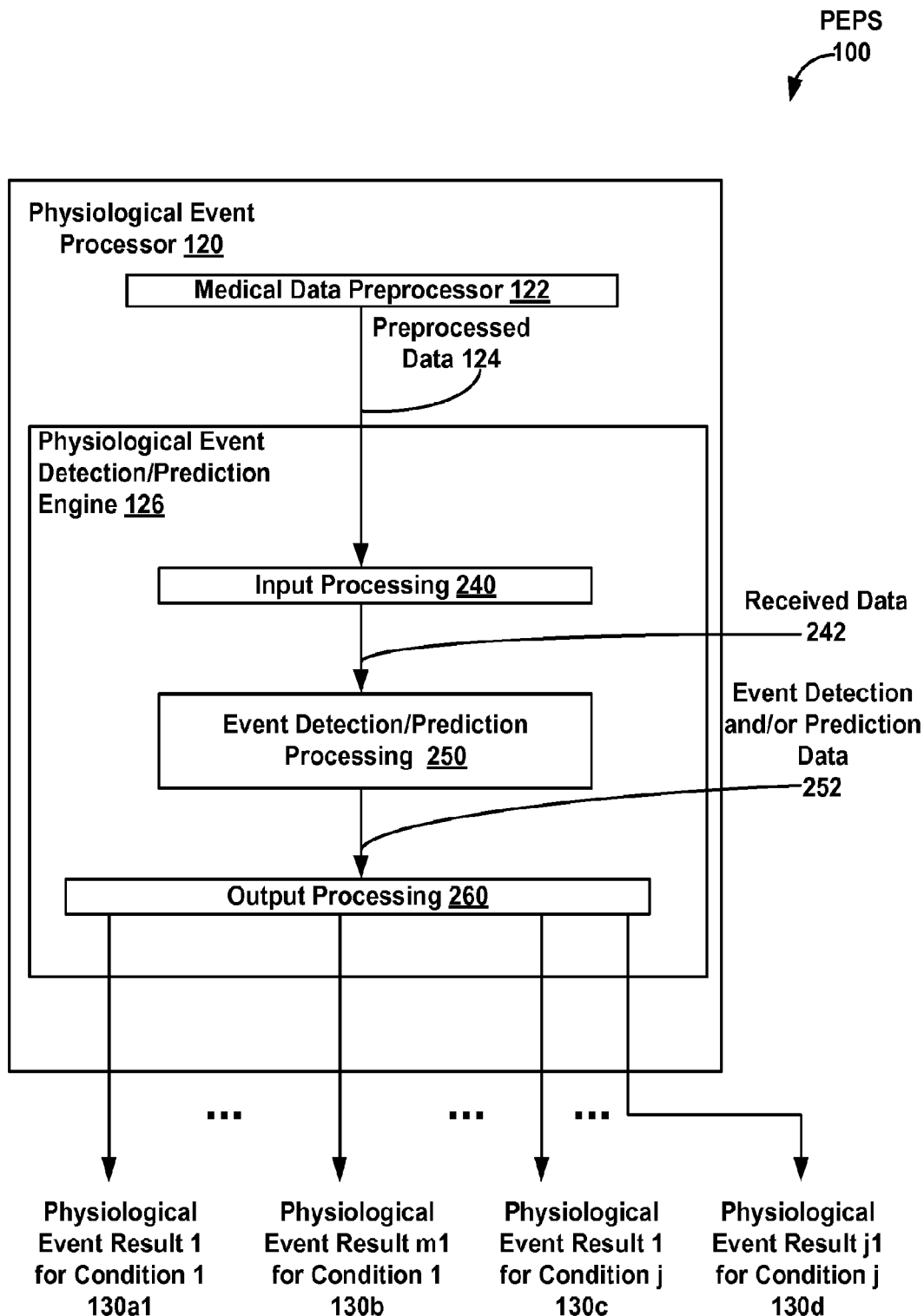
FIG. 2B is a block diagram of an exemplary physiological event detection/prediction engine.

FIGS. 2A and 2B show additional details of physiological event processor 120 of physiological event processing system 100. FIG. 2A shows a block diagram of an exemplary data preprocessor 122 with data segmenter 210, data transformer 220, and data encoder 230. Data segmenter 210 can be configured to receive physiological data from one or more data sources. FIG. 2A shows data segmenter 210 receiving data from n input data sources 110a-110n.

Data segmenter 210 segments physiological data. In some embodiments, segmenting data includes dividing the data into "segments" or blocks of data of representing information from a particular input data source for a pre-determined duration (i.e., amount of time). For example, data from a medical device, such as an electrocardiograph (EKG) or electroencephalograph (EEG), are segmented into blocks of data representing 30-second intervals of EKG or EEG data.

In some embodiments, a segment includes other information along with a block of data from an input data source. In some embodiments, a segment includes information identifying a patient monitored by the input data source and/or identifying a particular data source that generated a corresponding block of data; e.g., an EKG or EEG. In some scenarios, corresponding timing information (start time, stop time, and/or duration information) and/or an identifier that uniquely identifies the segment are included with the segment. An example unique identifier for a segment can be constructed by concatenation of patient identification, data source, and timing information for the segment.

As shown in FIG. 2A, the generated segments are passed as segmented data 212 to data transformer 220. In particular embodiments, data transformer 220 is configured to apply one or more transformations to the segments of segmented data 212. Example transformations include application of Fourier transform(s), wavelet transform(s), chirplet transform(s), and/or other transform(s) to the block of data. In some embodiments, data transformer 220 gathers statistics of a transformed segment as well; e.g., frequency maxima and/or minima values. In some scenarios, each transformed segment and/or statistics for transformed segment(s) are part of transformed data 222.

FIG. 2A shows transformed data 222 sent from data transformer 220 to data encoder 230. Data encoder 230 encodes transformed data 222 into a format suitable for use by physiological event detection/prediction engine 126. Example formats included binary formats, textual (alphanumeric) formats, graphical formats, audio formats, and/or other formats. FIG. 2A shows the resulting encoded data sent as preprocessed data 124 to physiological event detection/prediction engine 126.

FIG. 2B shows a block diagram of an exemplary physiological event detection/prediction engine 126. Physiological event detection/prediction engine 126 applies input processing 240 to the received preprocessed data 124. In some embodiments, input processing 240 includes selecting and/or weighting of preprocessed data 124. In these embodiments, the selection and/or weighting is performed by storing input coefficients in an input weighting matrix and performing a matrix-vector multiplication between the input weighting matrix and preprocessed data 124 (treated as a vector) to generate a vector to act as received data 242.

After applying input processing 240 to preprocessed data 124, received data 242 are provided to event detection/prediction processing 250. Event detection/prediction processing 250 can be configured to examine received data 242 for patterns related to physiological events. As such, event detection/prediction processing 250 can be performed by a suitably trained neural network, a genetic algorithm, an expert system, one or more digital signal processors, and/or other computer software and/or hardware designed to detect and/or predict physiological events.

After performing event detection/prediction processing 250, event detection/prediction data 252 is provided to output processing 260. In some embodiments, the event detection/prediction data 252 is weighted by an output weighting matrix by output processing 260 using similar techniques to those discussed above with respect to the input weighting matrix.

Upon performing output processing 260, one or more physiological event results 130a-130d are output for each of one or more conditions. FIG. 2B shows output processing 260 generating outputs for a number j of conditions, where a number m1 of physiological event results are output for condition 1 and a number j1 of physiological event results are generated for condition j. Example physiological event results 130a-130d include, but are not limited to, informative physiological event results and directive physiological event results as described above in more detail with respect to FIG. 1.

An Exemplary Computing Device

Figure 3:
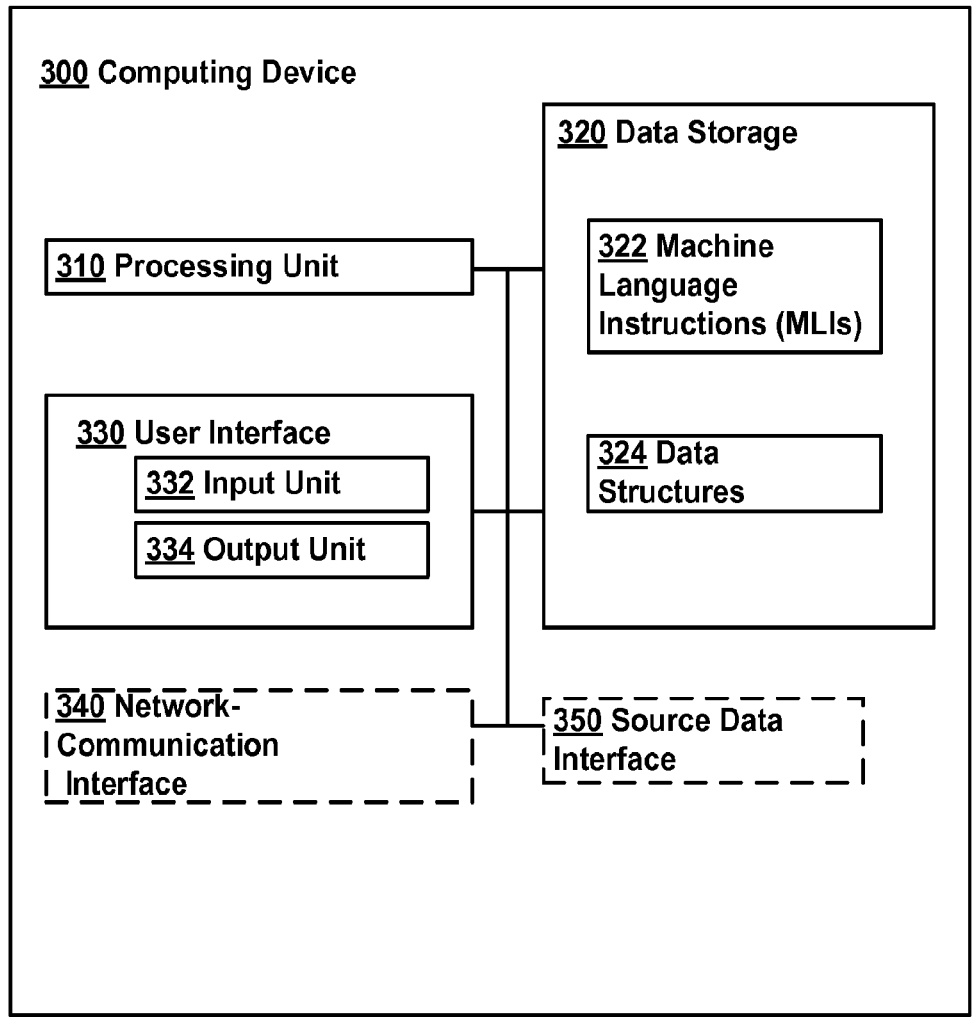
FIG. 3 is a block diagram of an exemplary computing device.

FIG. 3 is a block diagram of an exemplary computing device 300, comprising processing unit 310, data storage 320, user interface 330, network-communication interface 340, and source data interface 350, in accordance with embodiments of the invention. Computing device 300 can be a desktop computer, laptop or notebook computer, personal data assistant (PDA), mobile phone, embedded processor, or any similar device that is equipped with at least one processing unit capable of executing machine-language instructions that implement at least part of the herein-described methods, including but not limited to method 1300 described in more detail below with respect to FIG. 13, and/or herein-described functionality of an input data source, a physiological event processor, a data preprocessor, a physiological event detection/prediction engine, an output device, a data segmenter, a data transformer, a data encoder, input processing, event detection/prediction processing, output processing, a data preprocessor, a segmenter, a wavelet transformer, a binary encoder, a LAMSTAR neural network, an input layer, a SOM node layer, and/or an output layer, Processing unit 310 can include one or more central processing units, computer processors, mobile processors, digital signal processors (DSPs), microprocessors, computer chips, and similar processing units configured to execute machine-language instructions and process data.

Data storage 320 comprises one or more storage devices with at least enough combined storage capacity to contain machine-language instructions 322 and data structures 324. Data storage 320 can include read-only memory (ROM), random access memory (RAM), removable-disk-drive memory, hard-disk memory, magnetic-tape memory, flash memory, and similar storage devices.

Machine-language instructions 322 and data structures 324 contained in data storage 320 include instructions executable by processing unit 310 and any storage required, respectively, to perform at least part of herein-described methods, including but not limited to method 1300 described in more detail below with respect to FIG. 13, and/or herein-described functionality of an input data source, a physiological event processor, a data preprocessor, a physiological event detection/prediction engine, an output device, a data segmenter, a data transformer, a data encoder, input processing, event detection/prediction processing, output processing, a data preprocessor, a segmenter, a wavelet transformer, a binary encoder, a LAMSTAR neural network, an input layer, a SOM node layer, and/or an output layer, The terms tangible computer-readable medium and tangible computer-readable media refer to any tangible medium that can be configured to store instructions, such as machine-language instructions 322, for execution by a processing unit and/or computing device; e.g., processing unit 310. Such a medium or media can take many forms, including but not limited to, non-volatile media and volatile media. Non-volatile media includes, for example, read only memory (ROM), flash memory, magnetic-disk memory, optical-disk memory, removable-disk memory, magnetic-tape memory, hard drive devices, compact disc ROMs (CD-ROMs), direct video disc ROMs (DVD-ROMs), computer diskettes, and/or paper cards. Volatile media include dynamic memory, such as main memory, cache memory, and/or random access memory (RAM). Many other types of tangible computer-readable media are possible as well. As such, herein-described data storage 320 can comprise and/or be one or more tangible computer-readable media.

User interface 330 comprises input unit 332 and/or output unit 334. Input unit 332 can be configured to receive user input from a user of computing device 300. Input unit 332 can comprise a keyboard, a keypad, a touch screen, a computer mouse, a track ball, a joystick, and/or other similar devices configured to receive user input from a user of the computing device 300.

Output unit 334 can be configured to provide output to a user of computing device 300. Output unit 334 can comprise a visible output device for generating visual output(s), such as one or more cathode ray tubes (CRT), liquid crystal displays (LCD), light emitting diodes (LEDs), displays using digital light processing (DLP) technology, printers, light bulbs, and/or other similar devices capable of displaying graphical, textual, and/or numerical information to a user of computing device 300. Output unit 334 alternately or additionally can comprise one or more aural output devices for generating audible output(s), such as a speaker, speaker jack, audio output port, audio output device, earphones, and/or other similar devices configured to convey sound and/or audible information to a user of computing device 300.

Optional network-communication interface 340, shown with dashed lines in FIG. 3, can be configured to send and receive data over a wired-communication interface and/or a wireless-communication interface. The wired-communication interface, if present, can comprise a wire, cable, fiber-optic link and/or similar physical connection to a data network, such as a wide area network (WAN), a local area network (LAN), one or more public data networks, such as the Internet, one or more private data networks, or any combination of such networks. The wireless-communication interface, if present, can utilize an air interface, such as a ZigBee, Wi-Fi, and/or WiMAX interface to a data network, such as a WAN, a LAN, one or more public data networks (e.g., the Internet), one or more private data networks, or any combination of public and private data networks. In some embodiments, network-communication interface 340 can be configured to send and/or receive data over multiple communication frequencies, as well as being able to select a communication frequency out of the multiple communication frequency for utilization.

Optional source data interface 350, shown in FIG. 3 with dashed lines, permits communication with one or more input data source devices. Exemplary input data source devices include polysomnograms, electrocardiograms (EKGs), electroencephalograms (EEGs), heart rate monitors, magnetic resonance imaging (MRI) devices, X-ray machines, thermometers and other temperature measuring devices, blood pressure devices, other pressure-detecting devices, volume measuring devices, blood chemistry devices, pressure transducers, thermocouples, electromyograms, electrooculograms, pulse oximeters, other oxygen and/or other gas sensors, movement sensors, scales, devices configured to provide data related to a patient, diagnostic devices, medical devices, and/or other devices. Many other types of source data devices are possible as well. In particular embodiments, the source data devices provide data related to physiological parameters.

Source data interface 350 can include a wired-sensor interface and/or a wireless-sensor interface. In some embodiments, the wired-sensor interface and the wireless-sensor interface utilize the technologies described above with respect to the wired-communication interface of network-communication interface 340 and the wireless-communication interface of network-communication interface 340, respectively. In other embodiments, one or more input device(s) communicate with computing device 300 via source data interface 350.

An Exemplary Embodiment of the Physiological Event Processing System

Figure 4:
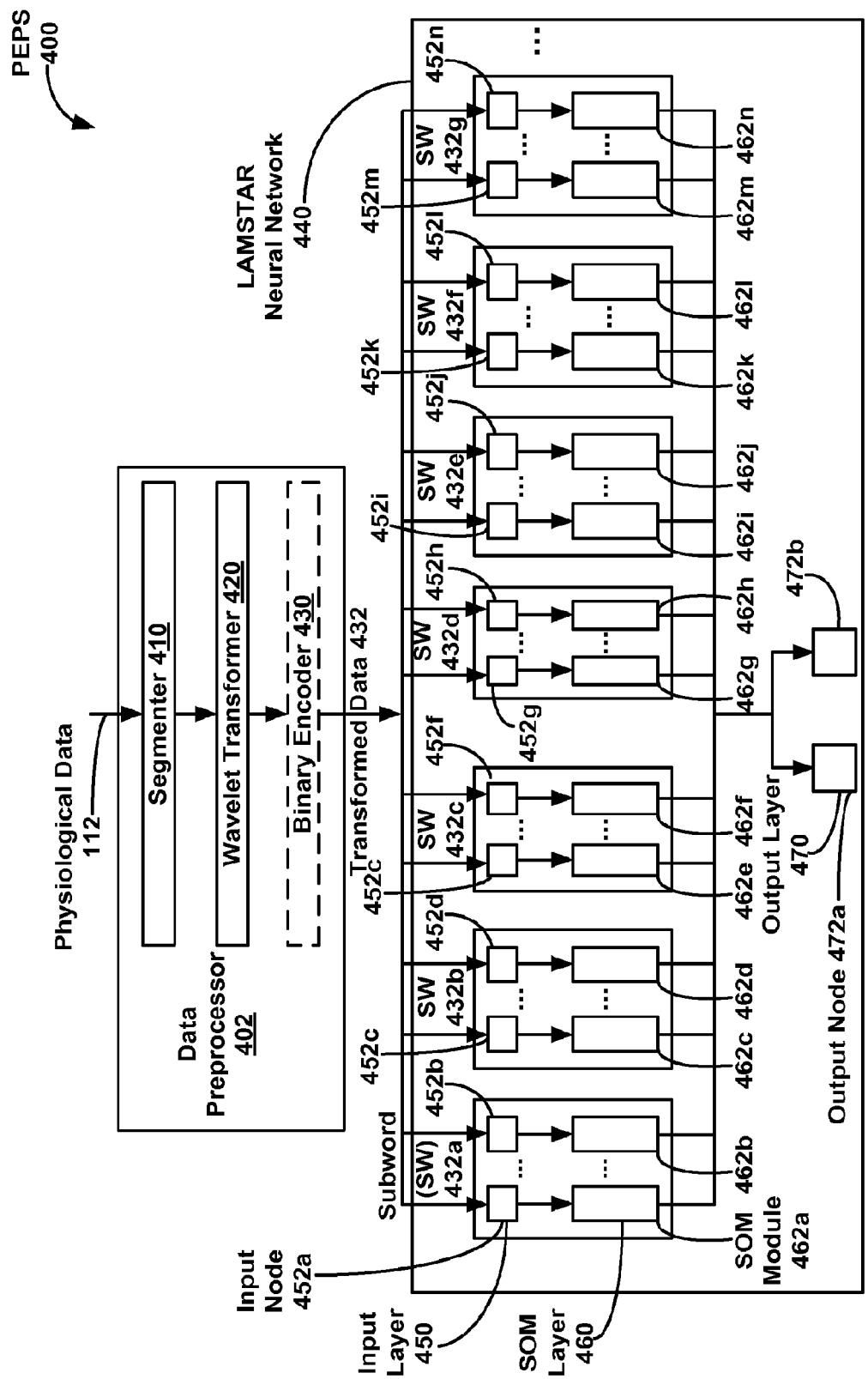
FIG. 4 is a block diagram of an exemplary physiological event processing system with a data preprocessor and a LArge Memory STorage And Retrieval (LAMSTAR) neural network.

FIG. 4 is a block diagram of an exemplary physiological event processing system 400 with a data preprocessor 402 and a LAMSTAR neural network 440. Data preprocessor 402 includes a segmenter 410 and wavelet transformer 420. Data preprocessor 402 may include an optional binary encoder 430, shown in FIG. 4 with dashed lines. LAMSTAR neural network 440 is shown in FIG. 4 with input layer 450, self-organizing map (SOM) layer 460, and output layer 470.

In particular embodiments, preprocessor 402 is configured to produce a set of inputs for LAMSTAR neural network 440 that capture the time-frequency spectral dynamics of physiological data 112. In some embodiments, segmenter 410 segments physiological data 112 based on time. For example, segmenter 410 can segment physiological data into 30, 60, 90, and/or 120 second data segments.

In particular embodiments, wavelet transformer 420 is configured to generate a set of statistics using a wavelet transform of segmented data generated by segmenter 410. Some embodiments of wavelet transformer 420 use a discrete wavelet transform of the Daubechies 4 family of wavelet functions. In other embodiments, wavelet transformer 420 uses another wavelet transform (e.g., Haar wavelets, higher-level families of wavelet functions, continuous wavelet transforms) and/or other similar transformation transforms/functions (e.g., short-time Fourier transforms, other Fourier transforms, Wigner transforms, multiresolution analysis).

In the particular embodiments, the wavelet transform used by wavelet transformer 420 is configured to provide information about the frequency content as a function of time for one or more segments in the segmented data. In the particular embodiments, wavelet transformer 420 is configured to apply a sliding window of differently scaled wavelet functions along the given segment. Wavelet transformer 420 can be configured to calculate a set of wavelet coefficients, or levels, for each scale of wavelet. Each wavelet level conveys the evolution of the correlation between the wavelet at that scale, or frequency band, and the given segment.

In particular embodiments, wavelet transformer 420 generates statistics for a given "raw" (pre-transformation) segment transformed into a transformed segment. Exemplary statistics include, but are not limited to:
- minimum amplitude values of the transformed segment at a given wavelet level,
- times (indices) of the minimum amplitude values at the given wavelet level,
- maximum amplitude values of the transformed segment at the given wavelet level,
- times/indices of the maximum amplitude values at the given wavelet level,
- a ratio between maxima and minima of the transformed segment at the given wavelet level,
- a root-mean-square (RMS) of the transformed segment at the given wavelet level, and/or
- a ratio of the RMS of the transformed segment to the RMS of the raw segment.

In these embodiments, binary encoder 430 is configured to encode each statistic in the set of statistics into binary codes. In the particular embodiments, binary encoder 430 computes histograms for each statistic. For example, the Freedman-Diaconis rule can be used to calculate an optimal bin width:

$$\text{Bin Width} = 2 * \text{IQR} * n^{-1/3} \quad (1)$$

where IQR is the inter-quartile range of the data, and n is the total number of data points. In some circumstances, Equation (1) can produce a zero bin width. In those cases, the Scott method can be used:

$$\text{Bin Width} = 3.49 * \sigma * n^{-1/3} \quad (2)$$

where $\sigma$ is the standard deviation of the data.

For each statistic, a common histogram for all segments is constructed. The histogram for the statistic is divided into a number of subsegments, perhaps after screening based on a threshold value of the statistic. For example, the area of the histogram in which all values exceeds a threshold of 10% of the maximum value of the statistic is located and then divided into five subsegments. Each subsegment boundary for a statistic is assigned a unique binary code. In particular embodiments, binary segmenter 430 identifies a subsegment in which a statistical value was located in its respective histogram and outputs the corresponding binary code for the statistical value. In these particular embodiments, transformed data 432 are a sequence of binary codes corresponding to histogram subsegments for each statistical value that are input to LAMSTAR neural network 440. In other embodiments, LAMSTAR neural network 440 does not use binary encoded data; in such embodiments, optional binary encoder 430 is not required to be part of data preprocessor 402.

LAMSTAR neural network 440 can be configured to handle large-scale storage-retrieval tasks while grossly capturing the input-output relationships of biological neural networks. In particular embodiments, LAMSTAR neural network 440 can be configured to learn a mapping between an arbitrary set of inputs, such as transformed data 432, and a set of outputs, shown in FIGS. 4, 5A, and 5B as output layer 470, using a supervised training process.

A portion of the architecture of LAMSTAR neural network 440 for processing transformed data 432, which includes statistics for each wavelet level of a single signal (i.e., input from a single data source) is schematically depicted in FIG. 4. In some embodiments, LAMSTAR neural network 440 contains identical structures for each signal.

Figure 5A:
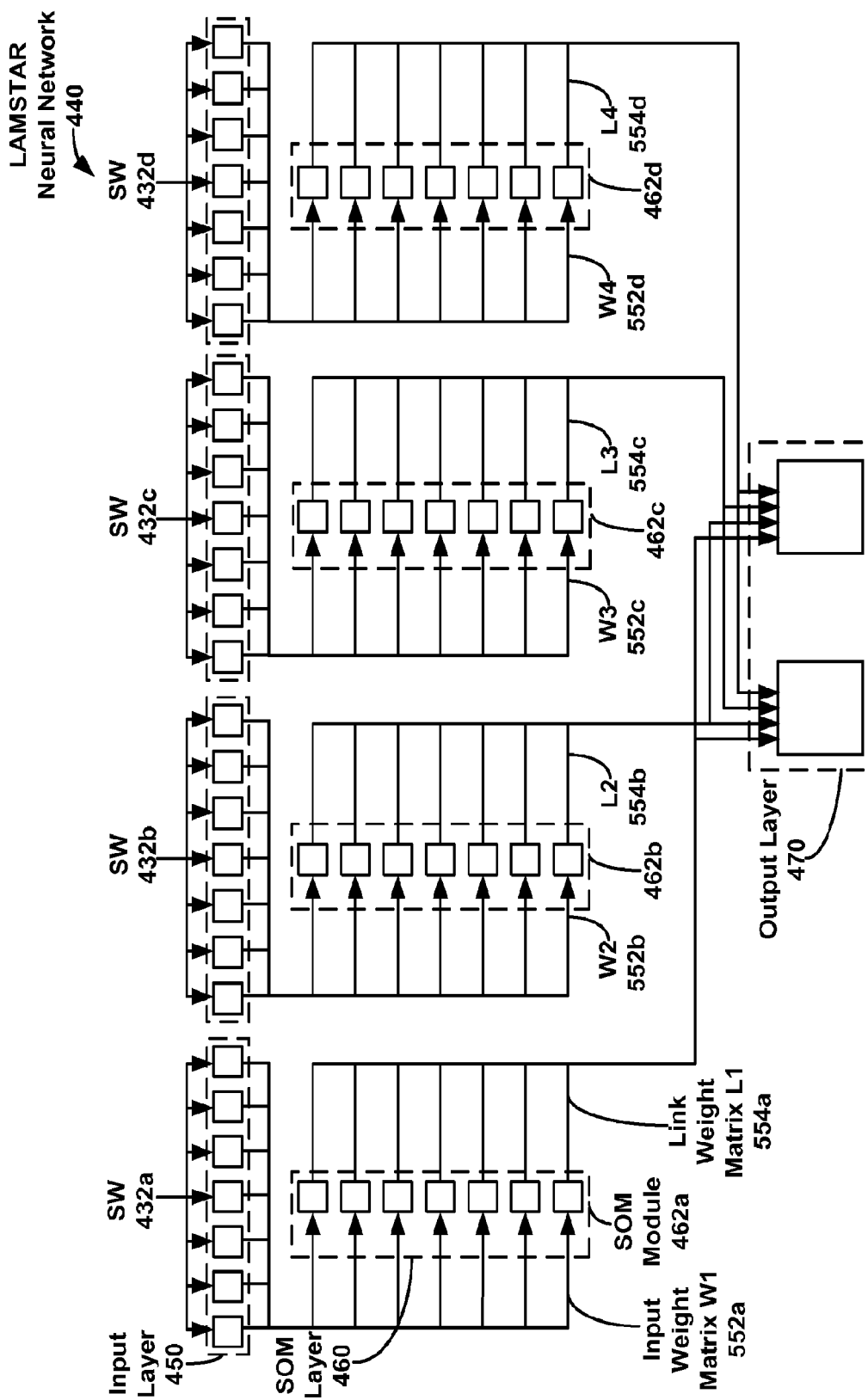
FIGS. 5A and 5B provide an expanded illustration of part of the LAMSTAR neural network.
Figure 5B:
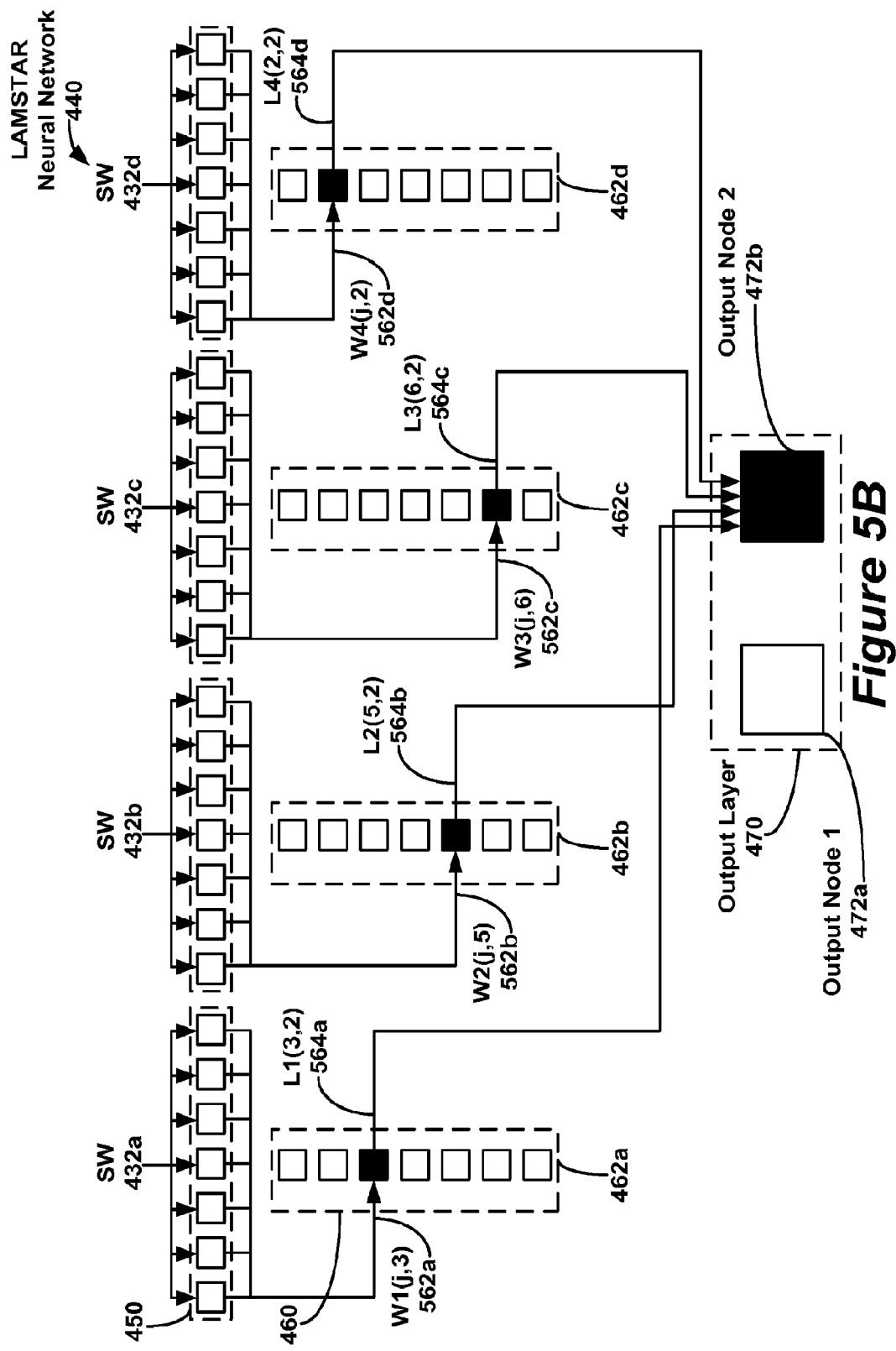

As illustrated in FIGS. 4, 5A, and 5B, LAMSTAR neural network 440 includes three types of nodes, arranged as layers. Input layer 450 receives input to LAMSTAR neural network 440 (i.e., transformed data 432) as an input word. FIG. 4 shows an input word of transformed data 432 composed of subwords (SWs) subwords 432a through 432g and presented to input nodes 452a through 452n in input layer 450. Each subword represents a separate attribute of transformed data 430. In some embodiments, each subword 432a-432g is a binary code corresponding to a histogram subsegment for each statistic for each wavelet level, generated by wavelet transformer 420, for each signal.

As shown in FIG. 4, one or more self-organizing map (SOM) modules 462a through 462n in SOM node layer 460 are associated with each subword. Each of the SOM modules 462a thorough 462n includes one or more SOM nodes. In particular embodiments, the SOM nodes of SOM modules 462a through 462n are arranged as one or more layers of SOM nodes.

FIG. 4 shows LAMSTAR neural network 440 with output layer 470. Output layer 470 consists of output nodes 472a and 472b. In some embodiments, output nodes 472a and 472b are fully interconnected with the SOM modules 462a-462n.

FIGS. 5A and 5B provide an expanded illustration of part of LAMSTAR neural network 440. For simplicity, only four input subwords 432a, 432b, 432c, and 432d and corresponding SOM modules 462a, 462b, 462c, and 462d are shown in FIGS. 5A and 5B. Each SOM module 462a, 462b, 462c, and 462d is shown in FIGS. 5A and 5B with seven SOM nodes. The seven SOM nodes are arranged into seven SOM sub-layers. In other embodiments than shown in FIGS. 5A and 5B, LAMSTAR neural network 440 includes SOM modules with fewer than seven SOM nodes or more than seven SOM sub-layers.

The links between input nodes in input layer 450 and SOM nodes in input SOM modules 462a-462d in input SOM layer 460 are weighted by the input-weight matrices $W_i$ and the links between input SOM node and output nodes are weighted by the matrices $L_i$. FIG. 5A shows the $W_i$ matrices as input-weight matrices W1 552a, W2 552b, W3 552c, and W4 552d and shows the $L_i$ matrices as link-weight matrices L1 554a, L2 554b, L3 554c, and L4 554d. Note that the solid lines in FIG. 5A represent one or more connections between individual nodes in input layer 450, input SOM layer 460, and/or output layer 470.

In operation, outputs of input nodes, each related to a subword, are fed into an associated input SOM module. The input SOM nodes operate using the following winner-takes-all rules as expressed in Equations (3) and (4) below:

$$S(i, k) = \sum_{j=1}^{N_i} W_i(j, k) \quad (3)$$

$$S(i, k_i^*) \geq S(i, k) \forall\, k \quad (4)$$

Equation 3 indicates that, for each input SOM node k in input SOM sub-layer i, the sum S(i, k) of the input-weights $W_i$ for input SOM node k is computed, where $N_i$ is the number of nodes in input SOM sub-layer i. Equation 4 indicates that, the input SOM node $k_i^*$ with the highest sum of input-weights over all input SOM nodes k for input SOM sub-layer i is the winning node for input SOM sub-layer i. Each winning SOM node represents the category the network has assigned to the associated subword. The set of all winning nodes represents the category the network has assigned to the entire input word.

By adjusting or training the input-weight matrices, $W_i$, each input SOM module can learn to classify its respective subword. In some embodiments, the input sub-words are predefined; e.g., binary codes generated by binary encoder 430. In such embodiments, the input-weight matrices $W_i$ are predefined to ensure a unique mapping between each input subword and corresponding input SOM node. In specific embodiments, predefined input-weight matrices $W_i$ are identity matrices of an appropriate size.

The output, or decision D(m*), of the LAMSTAR network is determined using Equations (5) and (6) below:

$$D(m) = \sum_{i=1}^{M} L_i(k_i^*, m) \quad (5)$$

$$D(m^*) \geq D(m) \forall\, m \quad (6)$$

where: M is the number of input SOM modules (layers),
m is an output node in the output (decision) layer, and $L_i(k_i^*,m)$ is the link weight between the winning node (denoted $k_i^*$) in the $i^{th}$ input SOM module and the $m^{th}$ output (decision) node. Hence the output node, denoted by m*, is the winning output node over all output nodes. Thus, the output node m* represents an output decision of LAMSTAR neural network 440 based on the input word.

FIG. 5B shows the link-weights and links associated with a scenario regarding a hypothetical set of winning SOM nodes. Upon the presentation of subwords 432a, 432b, 432c, and 432d to input nodes 450 of LAMSTAR neural network 440, each SOM module 462a, 462b, 462c, and 462d determines a winning node. In this scenario, SOM module 462a has chosen a third node, depicted in black in FIG. 5B, as the winning node. The winning node is chosen, as described above, based on the input-weight matrix and the link-weight matrix for each SOM module. As shown in FIG. 5B, input-weight matrix entry W1(j,3) and link-weight matrix entry L1(3,2) are the input-weight and link-weight associated with the winning node in SOM module 462a.

Similarly, FIG. 5B shows that a winning node for SOM module 462b is a fifth node of SOM module 462b, a winning node for SOM module 462c is a sixth node of SOM module 462c, and a winning node for SOM module 462d is a second node of SOM module 462d. FIG. 5B also shows the related input-weight matrix and link-weight matrix values associated with the winning nodes of SOM modules 462b, 462c, and 462d. Further, FIG. 5B shows the winning node in output layer 470 is output node 2 472b.

Each node in the output layer indicates a different result. As an example, output node 1 472a can indicate a prediction that a patient will not experience a physiological event and output node 2 472b can indicate a prediction that a patient will experience the physiological event.

"Most Significant" Nodes of a LAMSTAR Neural Network

As mentioned above, the winning output node has the highest sum of link-weights in link-weight matrix L that connect that output node to the winning SOM nodes. Therefore, the link-weight matrix L of interconnections between memory-storing nodes of LAMSTAR neural network 440 and various layers or modules directly and meaningfully relates to physiological data 112. The link-weights are configured to be tracked in real-time to indicate precisely how and why LAMSTAR neural network 440 makes decisions. In some scenarios, the link-weight matrix L is used to determine the structure of physiological data 112 as presented to LAMSTAR neural network 440.

The most significant node (MSN) is defined as the SOM node or set of SOM nodes that have the highest link-weight to a particular output node m. That is, where $$L_i^*(k^*,m) \geq L_i(k,m) \forall i,k \qquad (7)$$

Similarly, the SOM nodes that have the second or third highest link-weights (second and third MSNs) can be determined. The MSNs indicate which input subwords (i.e., signal features) were most important for making a particular decision. In particular, the MSNs that have the largest difference between the link from a SOM node to one output node and the link from the same SOM node to the other output node are identified. This eliminates nodes in common between both outputs to choose MSNs most associated with a particular decision. Determining sets of the most significant nodes (e.g., the set of MSNs, or the set of first, second, and third MSNs) allows for identification of important signals and signal features for physiological events.

LAMSTAR Neural Network Training Examples

In particular embodiments, link-weights in the link-weight matrix L between nodes in SOM layer 460 and output nodes 470 are adjusted by numerical values representing punishments and rewards depending on the response of the network to the input word. For example, when LAMSTAR neural network 440 produces a desired output, link-weights in the link-weight matrix L from each winning SOM node to a correct output node are incremented (rewarded). When LAMSTAR neural network 440 produced an incorrect output, link-weights in the link-weight matrix L from each winning SOM node to the incorrect output node are decremented (punished), and link-weights from each winning SOM node to the correct output node are incremented. In some of the particular embodiments, the increments and decrements are of the same magnitude; e.g., rewards involve an increment of 1 and punishments involve a decrement of 1.

Thus, the operation of LAMSTAR neural network 440 includes:

1. Receiving an input word consisting of a set of subwords at LAMSTAR neural network 440.
2. Determining winning nodes for each SOM module according to winner-take-all rules; e.g., the rules expressed in Equations (3) and (4) above.
3. Summing the link-weights from the winning SOM nodes to each output node; e.g., using Equation (5).
4. Determining the output node with the highest sum of SOM-output link-weights; e.g., using Equation (6).
5. Adjusting the SOM-output link-weights according to the above-mentioned training rules regarding rewards and punishments.

The order in which inputs are presented to LAMSTAR neural network 440 during training can affect subsequent performance. This is because, as with biological neural networks, the order of presentation can favor the reinforcement of certain features and the degradation of others.

This is particularly true if different output categories share features. For instance, suppose LAMSTAR neural network 440 is trained on a successive set of inputs of Type A. By reinforcing some set of link-weights, LAMSTAR neural network 440 will learn to associate Type A inputs with the output node designated for Type A outputs. Now suppose a set of Type B inputs are presented to LAMSTAR neural network 440 for Type B prediction. In some scenarios, the Type B inputs share features with the Type A inputs (i.e., some of the Type B inputs are uncorrelated with a condition related to the Type B inputs). In such scenarios, LAMSTAR neural network 440 will, at first, classify Type B inputs as Type A until the features that differ between the two are sufficiently learned.

Later, if another set of Type A inputs are presented to LAMSTAR neural network 440, the features common to Types A and B will again be reinforced. If enough Type A inputs are successively presented, the sum of the link-weights that encode common features of Types A and B can exceed the sum of the link-weights that encode differing features between Types A and B. In such scenarios, the "memory" of differences between Type A and Type B can be degraded, and the performance of LAMSTAR neural network 440 can suffer in differentiating between Type A and Type B inputs. In this example, one technique to avoid such memory degradation is to alternately present Type A and Type B inputs during the training phase of LAMSTAR neural network 440.

To ensure that LAMSTAR neural network 440 is adequately trained, the accuracy of LAMSTAR neural network 440 is computed based on the number of training inputs used. In some embodiments, LAMSTAR neural network 440 is considered to be fully trained once the computed accuracy indicates asymptotic performance was achieved. See Tables 7, 8, 9, and 10 for numbers of segments used to train LAMSTAR neural network 440 in different scenarios.

Exemplary Use of the Physiological Event Processor to Predict and Detect of Sleep-Related Physiological Events FIGS. 6A through 12B relate to an exemplary use of physiological event processor 400 as applied to sleep-related physiological events. In particular, physiological event processor 400 can be configured to generate physiological event results including detection and prediction of sleep apnea syndrome and hypopnea events. The physiological event processor 400 can be configured to detect and predict sleep-related physiological events in real time, as well as in near-real time and/or non-real-time scenarios. In some embodiments, the physiological event processor 400 is configured to detect and/or predict apnea and hypopnea events 30 to 120 seconds in advance. As part of prediction of sleep apnea syndrome and hypopnea events, an estimated proximity to an impending event is determined in some embodiments. Further, examination of LAMSTAR neural network 440 indicates which signals were most important for event prediction.

Exemplary Sleep Study Data

Overnight polysomnogram data were collected from 21 women and 53 men (average±standard deviation age was 48.1±10.8 years) with known or suspected obstructive sleep apnea syndrome. All subjects were treatment naïve or had discontinued CPAP at least 7 days prior to polysomnography. None had a history of surgical treatment for obstructive sleep apnea syndrome, bariatric surgery, or medically-managed weight loss intervention. Subjects arrived at the Sleep Center at 8 PM and were connected to a standard clinical recording montage. Subjects went to bed at 11 PM and were awoken at 7 AM. Recording was performed continuously throughout the night. Polysomnograms were scored by trained individuals using standard criteria. Apnea severity ranged from mild to severe, with an average±standard deviation apnea-hypopnea index (abnormal respiratory events per hour) of 36.8±30.5.

Figure 6A:
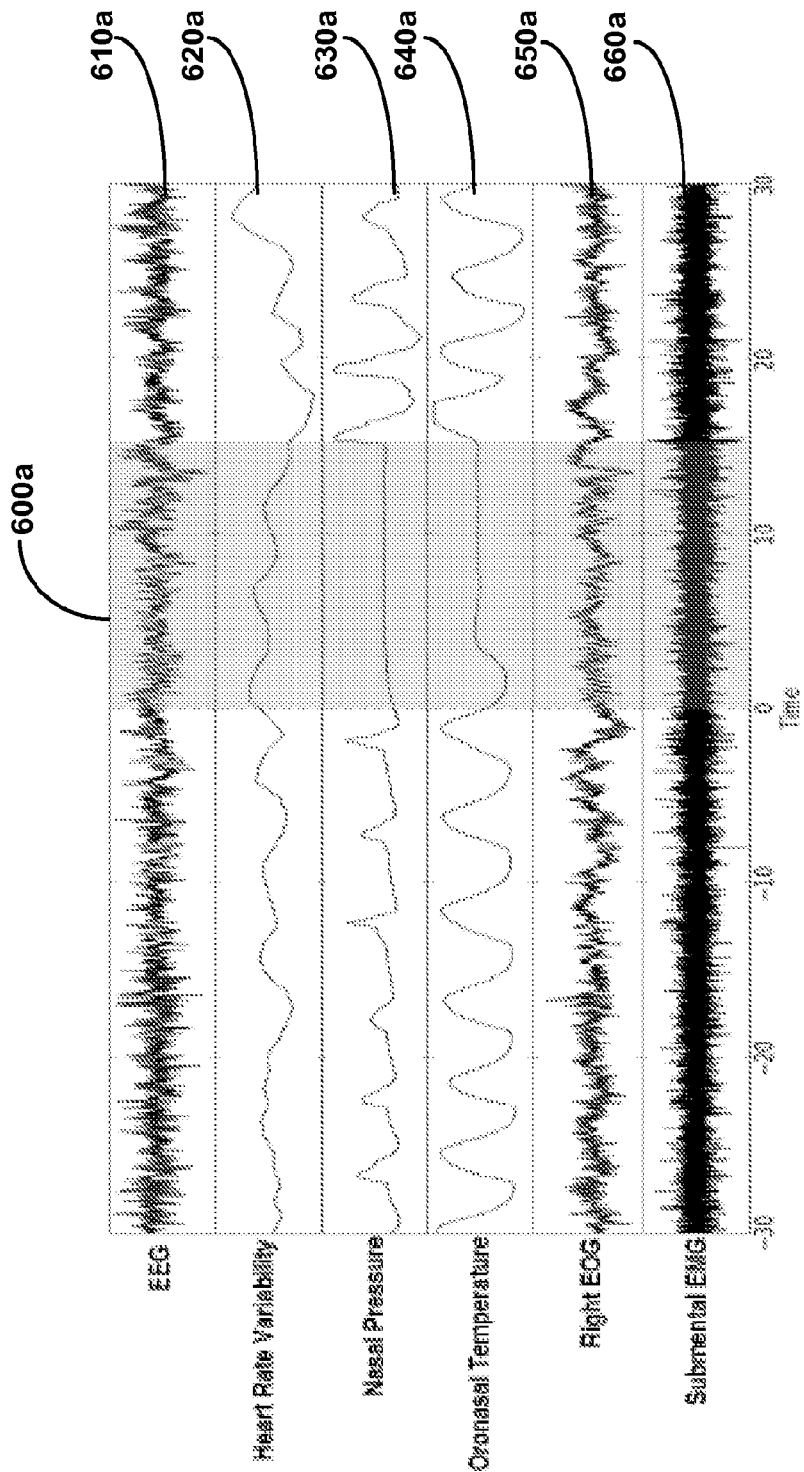
FIGS. 6A and 6B show exemplary signals extracted from a polysomnogram (PSG)
Figure 6B:
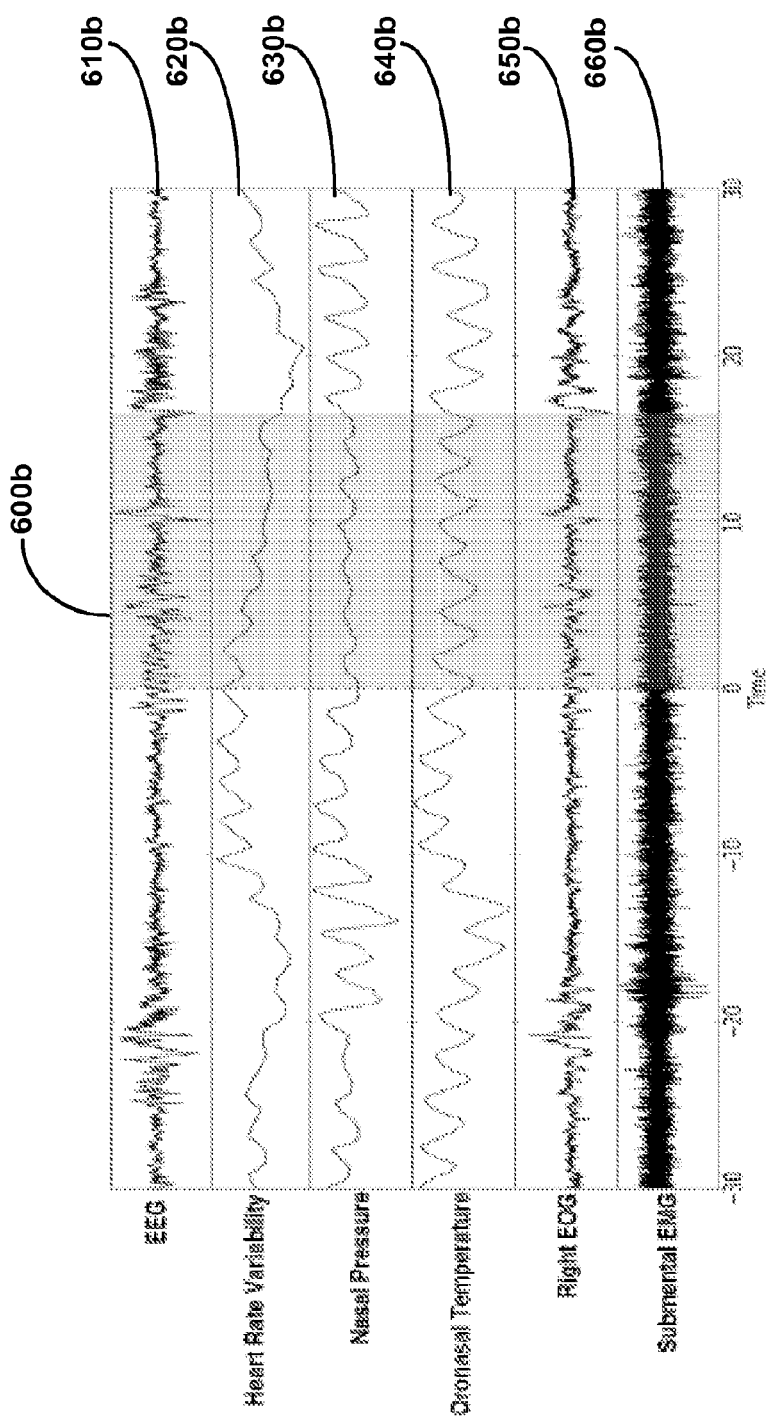

FIGS. 6A and 6B show example signals 600a and 600b, respectively extracted from a polysomnogram. Signals 600a detect an apnea episode during an interval outlined using a grey bar in FIG. 6A. Signals 600b detect a hypopnea episode during an interval outlined using a grey bar in FIG. 6B.

Signals 600a include electroencephalography signals (EEG) 610a, heart rate variability (HRV) signals 620a, nasal pressure signals 630a, oronasal temperature signals 640a, submental electromyography (EMG) signals 650a, and right electrooculography (EOG) signals 660a. Similarly, signals 600b include EEG signals 610b, HRV signals 620b, nasal pressure signals 630b, oronasal temperature signals 640b, EMG signals 650b, and right EOG signals 660b. In particular, right EOG signals 660a and 660b are measurements of a right eye of a patient.

Preprocessing of Sleep Study Data

Signals such as example signals 600a and 600b are presented to physiological event preprocessor 400 and then preprocessed. For testing prediction, segmenter 410 extracted data segments of 30, 60, 90, and 120 seconds in duration that contained a scored isolated apnea or hypopnea or the first event in a series. Segments of equal duration preceding each event were also extracted. Finally, segments of each duration containing normal breathing, defined as the absence of scored respiratory events regardless of the presence of snoring, were extracted. Segments containing snoring were chosen as snoring is a common natural context within which apnea/hypopnea prediction and detection must be performed. For testing detection, all 30-second segments containing a scored apnea or hypopnea were extracted. Segmenter 410 also normalized each signal from each segment by dividing data within a segment by the mean value of the segment.

Wavelet transformer 420 applied a discrete wavelet transform, such as the Daubechies 4 wavelet transform, to each segment generated by segmenter 410. The resulting transformed segments included a set of new signals, called levels, each of which quantified the frequency content of the original signal for a different frequency band as a function of time. For each level, wavelet transformer calculated the amplitude and timing for each of the three minima and three maxima, the ratio between the mean of the three maximum amplitudes and the mean of three minimum amplitudes, the root-mean-square value, and the root-mean-square value relative to that of the original signal.

Binary encoder 430 generated binary codes related to the transformed segments suitable for use with LAMSTAR neural network 440 as described above with respect to FIG. 4.

Training and Testing

For each segment duration, separate LAMSTAR neural networks 440 were trained to predict sleep-related physiological events for varying lead times (30, 60, 90, and 120 seconds into the future) and to detect sleep-related physiological events. To train networks, random sets containing equal numbers (117 to 583) of apnea/hypopnea segments and normal segments were constructed. Based on network responses to training inputs, incremental adjustments were made to the link-weights of each LAMSTAR neural network allowing convergence to optimal network performance.

Once a network was trained, 50 random test sets of different data segments were constructed, and average±SD sensitivities, specificities, positive predictive values, and negative predictive values for event prediction and event detection were determined. Statistical tests were performed using unequal variance T-tests.

Apnea and Hypopnea Prediction: Varying Segment Duration

Figure 7B:
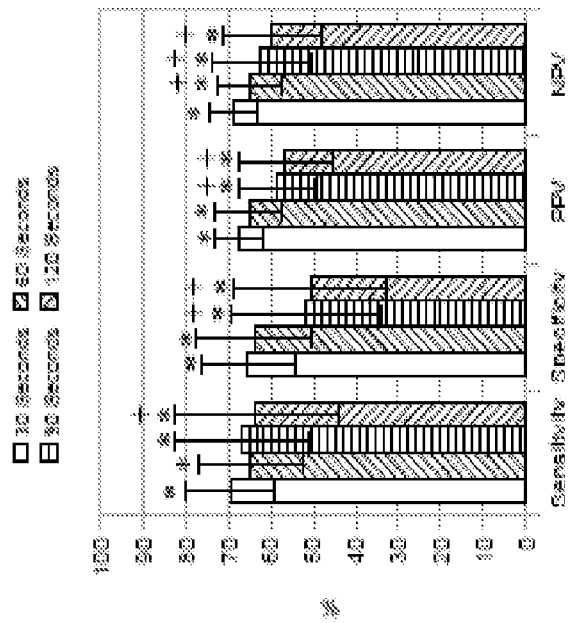
FIGS. 7A and 7B show results of sleep apnea syndrome prediction during Non-Rapid Eye Movement (NREM) sleep and Rapid Eye Movement (REM) sleep, respectively.
Figure 7A:
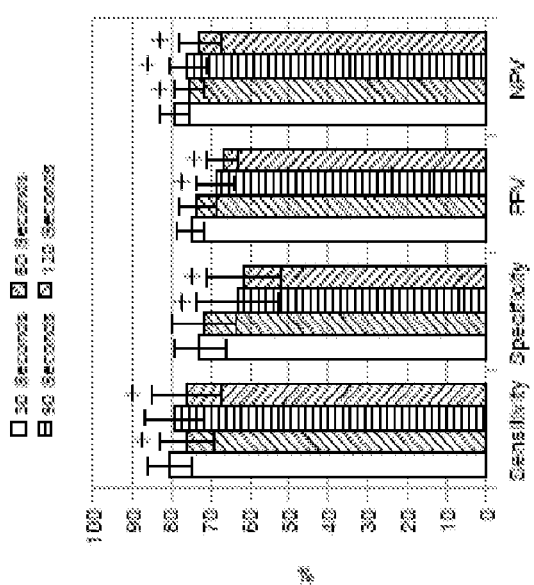

FIGS. 7A and 7B show results of sleep apnea syndrome prediction during Non-Rapid Eye Movement (NREM) and Rapid Eye Movement (REM), respectively. For apnea prediction using 30-second segments and a 30-second lead time during NREM sleep, the sensitivity was 80.6±5.6%, the specificity was 72.78±6.6%, the positive predictive value (PPV) was 75.1±3.6%, and the negative predictive value (NPV) was 79.4±3.6%. REM apnea prediction demonstrated a sensitivity of 69.3±10.5%, a specificity of 67.4±10.9%, a PPV of 67.4±5.6%, and a NPV of 68.8±5.8%.

The most significant nodes of LAMSTAR neural network 440 were analyzed. Based on the most significant node analysis, the most important signal for predicting apnea using 30-second segments and distinguishing an impending apnea from normal breathing is a submental electromyogram signal. Specifically, the most important feature of the submental electromyogram signal is a root-mean-square value of a first wavelet level. For predicting apnea using 60-second segments, nasal pressure was also an important signal. See Tables 1, 2, and 3 below for additional details regarding most significant nodes used for apnea predictions.

Figure 8B:
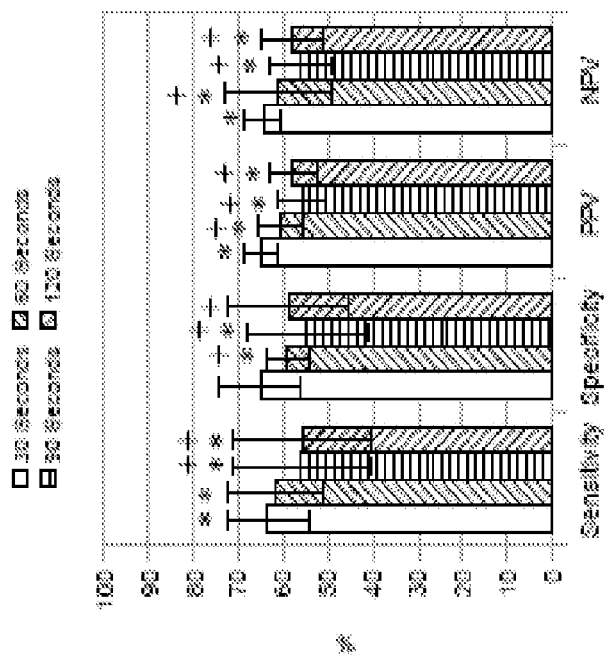
FIGS. 8A and 8B show results of hypopnea prediction during NREM sleep and during REM sleep, respectively.
Figure 8A:
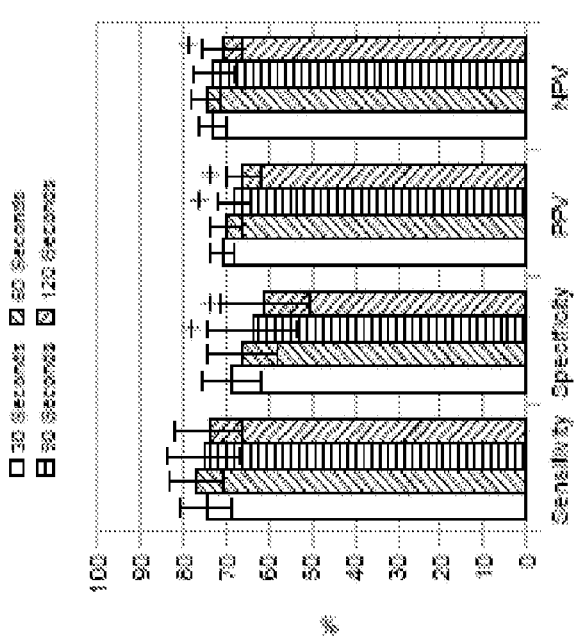

FIGS. 8A and 8B show results of hypopnea prediction during NREM sleep and during REM sleep, respectively. During NREM sleep, hypopnea prediction using 30-second segments and a 30-second lead time had a sensitivity of 74.4±5.9%, a specificity of 68.8±7.0%, a PPV of 70.8±3.1%, and a NPV of 73.2±3.1%. REM hypopnea prediction had a sensitivity of 63.4±9.2%, a specificity of 65.1±9.3%, a PPV of 65.0±4.0%, and a NPV of 64.5±4.0%.

Based on a most significant node analysis of LAMSTAR neural networks, the most important signals for predicting hypopnea in 30-second segments and distinguishing hypopnea from normal breathing were determined to be heart rate variability and submental electromyogram signals. The most important heart rate variability signal feature was a relative root-mean-square value of a first wavelet level. The most important submental electromyogram signal feature was a root-mean-square value of a first wavelet level. For predicting hypopnea in 60-second segments, the most important signal was nasal pressure. See Tables 4, 5, and 6 below for additional details regarding most significant nodes used for hypopnea predictions.

Figure 9B:
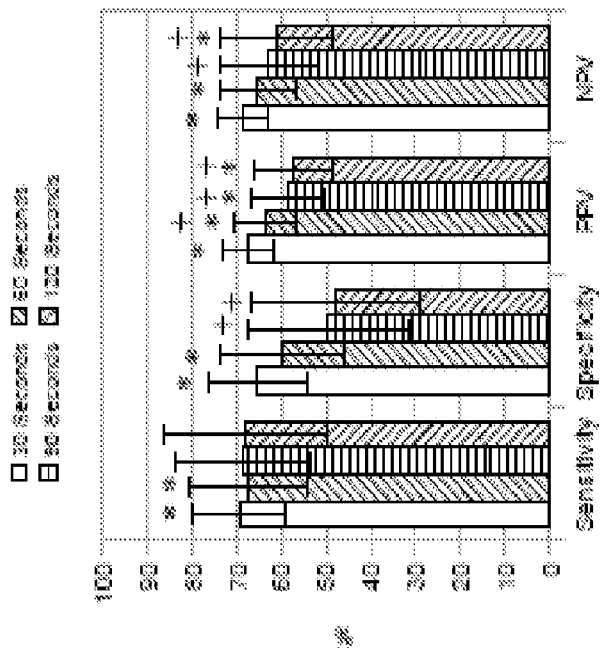
FIGS. 9A and 9B show results of sleep apnea syndrome prediction for varying prediction lead times during NREM sleep and REM sleep, respectively.
Figure 9A:
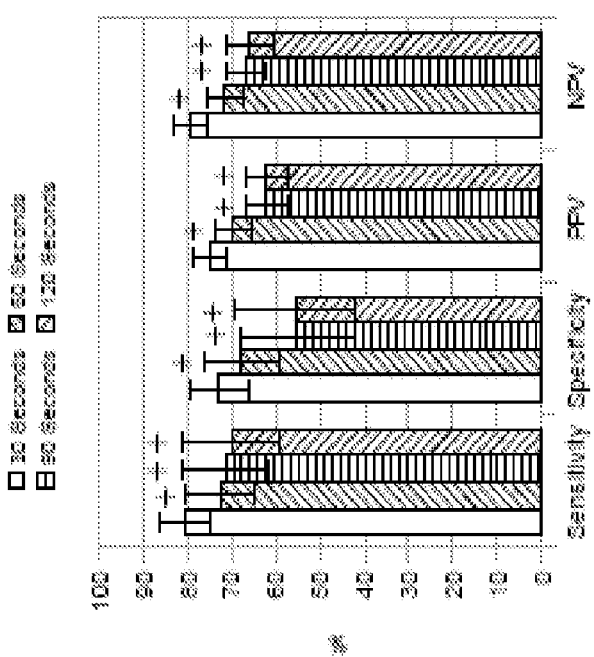

FIGS. 9A and 9B show results of sleep apnea syndrome prediction for varying prediction lead times during NREM sleep and REM sleep, respectively. As would be expected, as the lead time increased, performance decreased. Apnea prediction was best for events occurring in the next 30 seconds.

Figure 10B:
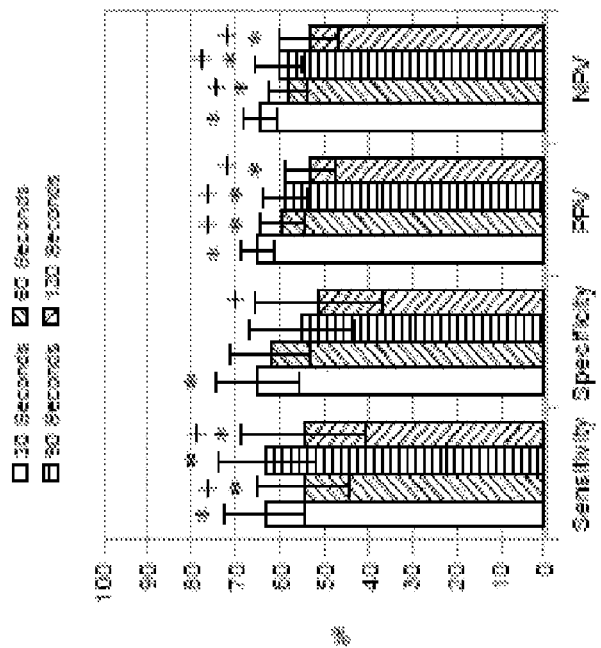
FIGS. 10A and 10B show results of hypopnea prediction for varying prediction lead times during NREM sleep and REM sleep, respectively.
Figure 10A:
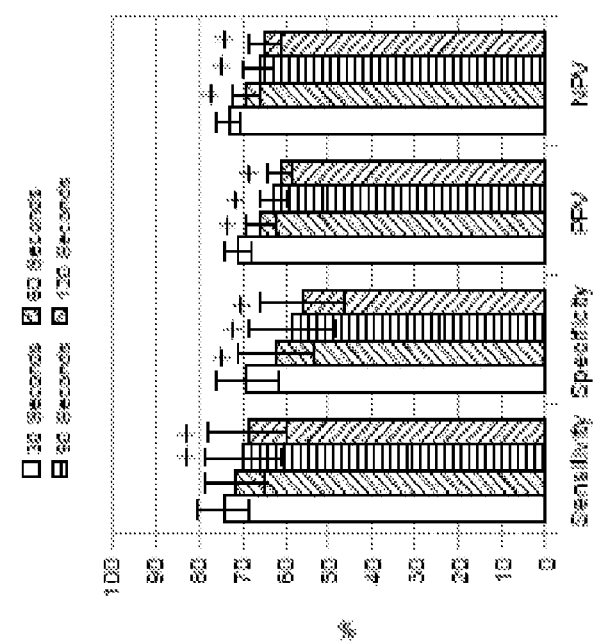

FIGS. 10A and 10B show results of hypopnea prediction for varying prediction lead times during NREM sleep and REM sleep, respectively. For hypopnea prediction, prediction using 30-second and 60-second lead times performed equally well.

Each most significant node reported in the tables is denoted by its associated signal name, signal feature name, wavelet level, and winning SOM node. The signals are electroencephalography (EEG), heart rate variability (HRV), nasal pressure, oronasal temperature, submental electromyography (EMG), and right electrooculography (EOG). The signal features are the indices of the maximum and minimum peaks in a signal, the amplitudes of maximum and minimum peaks in the signal, the root-mean-square (RMS) value of a signal, and a "relative RMS" value, which is the RMS value of a signal at a wavelet level relative to the RMS value of the signal.

The most frequent first, second, and third most significant nodes for apnea and hypopnea prediction and detection are indicated in Tables 1-6 below. Tables 1 and 2 show results for LAMSTAR neural networks 440 trained to distinguish normal breathing from obstructive sleep apnea syndrome and to make apnea predictions using 30-second and 60-second long segments, respectively. Table 1 also shows results for apnea predictions 30 seconds in the future ("30-Second Lead Times"). Table 3 shows results for apnea predictions and 60 seconds into the future ("60-Second Lead Times").

TABLE 1

Apnea Prediction Using 30-Second Segments and for 30-Second Lead Times

| Output | Most Significant Node | Signal Feature for Most Significant Node | Frequency |
|---|---|---|---|
| Normal Breathing | First | EMG RMS, Level 1, Node 1 | 74% |
| | Second | EMG, maximum peak amplitudes, Level 1, Node 2 | 22% |
| | Third | EMG, maximum peak amplitudes, Level 1, Node 2 | 12% |
| Apnea Prediction | First | EMG RMS, Level 1, Node 6 | 78% |
| | Second | EMG RMS, Level 2, Node 6 | 22% |
| | Third | EMG RMS, Level 2, Node 6 | 20% |

TABLE 2

Apnea Prediction Using 60-Second Segments

| Output | Most Significant Node | Signal Feature for Most Significant Node | Frequency |
|---|---|---|---|
| Normal Breathing | First | Nasal pressure, indices of maximum peak amplitudes, Level 6, Node 5 | 78% |
| | Second | Nasal pressure, indices of maximum peak amplitudes, Level 6, Node 5 | 38% |
| | Third | Oronasal temperature, indices of maximum peak amplitudes, Level 6, Node 3 | 20% |
| Apnea Prediction | First | EMG RMS, Level 1, Node 6 | 60% |
| | Second | Nasal pressure, minimum peak amplitudes, Level 5, Node 3 | 18% |
| | Third | EMG RMS, Level 1, Node 6 | 14% |

TABLE 3

Apnea Prediction for 60-Second Lead Times

| Output | Most Significant Node | Signal Feature for Most Significant Node | Frequency |
|---|---|---|---|
| Normal Breathing | First | EMG RMS, Level 1, Node 1 | 26% |
| | Second | EMG RMS, Level 1, Node 1 | 18% |
| | Third | EMG RMS, Level 2, Node 2 | 16% |
| Apnea Prediction | First | EMG RMS, Level 1, Node 6 | 56% |
| | Second | EMG RMS, Level 2, Node 6 | 34% |
| | Third | EMG RMS, Level 2, Node 6 | 12% |

Table 3

Tables 4 and 5 show results for LAMSTAR neural networks 440 trained to distinguish normal breathing from hypopnea to make hypopnea predictions using 30-second and 60-second long segments, respectively. Table 4 also shows results for 30-second lead time apnea predictions. Table 6 shows results for 60-second lead time apnea predictions.

TABLE 4

Hypopnea Prediction for 30-Second Segments and for 30-Second Lead Times

| Output | Most Significant Node | Signal Feature for Most Significant Node | Frequency |
|---|---|---|---|
| Normal Breathing | First | EMG RMS, Wavelet Level 1, Subword 1, Node 1 | 92% |
| | Second | EMG maximum peak amplitudes, Level 2, Subword 2, Node 2 | 30% |
| | Third | EEC RMS, Level 1, Subword 1, Node 1 | 32% |
| Hypopnea Prediction | First | HRV Relative RMS, Level 1, Subword 1, Node 1 | 58% |
| | Second | HRV Relative RMS, Level 1, Subword 1, Node 1 | 28% |
| | Third | EMG Relative RMS, Level 7, Subword 1, Node 6 | 16% |

TABLE 5

Hypopnea Prediction Using 60-Second Segments

| Output | Most Significant Node | Signal Feature for Most Significant Node | Frequency |
|---|---|---|---|
| Normal Breathing | First | Nasal pressure, indices of maximum peak amplitudes, Level 6, Node 5 | 94% |

TABLE 5-continued

Hypopnea Prediction Using 60-Second Segments

| Output | Most Significant Node | Signal Feature for Most Significant Node | Frequency |
|---|---|---|---|
| | Second | Nasal pressure, indices of maximum peak amplitudes, Level 6, Node 5 | 42% |
| | Third | EMG RMS, Level 1, Node 1 | 34% |
| Hypopnea Prediction | First | Nasal pressure, indices of minimum peak amplitudes, Level 5, Node 3 | 24% |
| | Second | EMG RMS, Level 1, Node 6 | 18% |
| | Third | Nasal pressure, indices of minimum peak amplitudes, Level 5, Node 3 | 14% |

TABLE 6

Hypopnea Prediction for 60-Second Lead Times

| Output | Most Significant Node | Signal Feature for Most Significant Node | Frequency |
|---|---|---|---|
| Normal Breathing | First | EMG RMS, Level 1, Node 1 | 78% |
| | Second | EEG RMS, Level 1, Node 1 | 18% |
| | Third | EMG, maximum peak amplitudes, Level 1, Node 4 | 16% |
| Hypopnea Prediction | First | EMG RMS, Level 2, Node 6 | 32% |
| | Second | EMG RMS, Level 1, Node 6 | 22% |
| | Third | EEG RMS, Level 1, Node 6 | 16% |

Tables 7-10 show total numbers of segments of physiological data used to train and test LAMSTAR neural network 440 for varying segment durations and lead times. Table 7 shows counts for the number of segments used to train and test LAMSTAR neural network 440 for sleep apnea syndrome prediction ranging over different segment durations.

TABLE 7

| Segment Duration | NREM Apnea Segment Count | NREM Normal Segment Count | REM Apnea Segment Count | REM Normal Segment Count |
|---|---|---|---|---|
| 30 | 454 | 20811 | 103 | 2643 |
| 60 | 322 | 10413 | 45 | 1340 |
| 90 | 250 | 6937 | 29 | 889 |
| 120 | 208 | 5222 | 26 | 667 |

The "NREM Apnea Segment Count" column of data in Table 7 indicates a number of segments used to train and test LAMSTAR neural network 440 based on physiological data recorded during non-rapid eye movement (NREM) sleep associated with sleep apnea syndrome. Similarly, the "NREM Normal Segment Count" column of data in Table 7 indicates a number of segments used to train and test LAMSTAR neural network 440 based on physiological data recorded during NREM sleep associated with normal breathing. Further, the "REM Apnea Segment Count" and "REM Normal Segment Count" columns of data in Table 7 indicate a number of segments used to train and test LAMSTAR neural network 440 based on physiological data recorded during rapid eye movement (REM) sleep associated with sleep apnea syndrome and normal breathing, respectively.

For example, Table 7 indicates that 454 30-second NREM apnea segments and 20811 30-second NREM normal segments trained LAMSTAR neural network 440 to predict obstructive sleep apnea syndrome during NREM sleep. Also, Table 7 indicates that 103 30-second REM apnea segments and 2643 30-second REM normal segments trained LAMSTAR neural network 440 to predict obstructive sleep apnea syndrome during REM sleep. Table 7 also shows counts for 60-second, 90-second, and 120-second long segments used to train LAMSTAR neural network 440.

Table 8 shows counts for the number of segments used to train and test LAMSTAR neural network 440 for sleep apnea syndrome prediction ranging over different lead times.

TABLE 8

| Lead Time | NREM Apnea Segment Count | NREM Normal Segment Count | REM Apnea Segment Count | REM Normal Segment Count |
|---|---|---|---|---|
| 30 | 454 | 20811 | 103 | 2643 |
| 60 | 322 | 20811 | 45 | 2643 |
| 90 | 250 | 20811 | 29 | 2643 |
| 120 | 208 | 20811 | 26 | 2643 |

For example, Table 8 indicates that 322 NREM apnea segments and 20811 NREM normal segments trained LAMSTAR neural network 440 to make predictions of obstructive sleep apnea syndrome during NREM sleep 60 seconds in advance.

Table 9 shows counts for the number of segments used to train and test LAMSTAR neural networks 440 for hypopnea prediction for different segment durations.

TABLE 9

| Segment Duration | NREM Hypopnea Segment Count | NREM Normal Segment Count | REM Apnea Segment Count | REM Normal Segment Count |
|---|---|---|---|---|
| 30 | 921 | 20811 | 246 | 2643 |
| 60 | 650 | 10413 | 154 | 1340 |
| 90 | 512 | 6937 | 111 | 889 |
| 120 | 426 | 5224 | 82 | 664 |

The "NREM Hypopnea Segment Count" column of data in Table 9 indicates a number of segments used to train and test LAMSTAR neural network 440 based on physiological data recorded during NREM sleep associated with hypopnea. Similarly, the "NREM Normal Segment Count" column of data in Table 9 indicates a number of segments used to train and test LAMSTAR neural network 440 based on physiological data recorded during NREM sleep associated with normal breathing. Further, the "REM Hypopnea Segment Count" and "REM Normal Segment Count" columns of data in Table 9 indicate a number of segments used to train and test LAMSTAR neural network 440 based on physiological data recorded during REM sleep associated with hypopnea and normal breathing, respectively.

For example, Table 9 indicates that 512 90-second NREM hypopnea segments and 6937 90-second NREM normal segments trained LAMSTAR neural network 440 to predict hypopnea during NREM sleep. Also, Table 9 indicates that 111 90-second REM apnea segments and 889 90-second REM normal segments trained LAMSTAR neural network 440 to predict hypopnea during REM sleep. Table 9 also shows counts for 30-second, 60-second, and 120-second long segments used to train LAMSTAR neural network 440.

Table 10 shows counts for the number of segments used to train LAMSTAR neural networks 440 for hypopnea prediction for different lead times.

TABLE 10

| Lead Time | NREM Apnea Segment Count | NREM Normal Segment Count | REM Apnea Segment Count | REM Normal Segment Count |
|---|---|---|---|---|
| 30 | 921 | 20811 | 246 | 2643 |
| 60 | 650 | 20811 | 154 | 2643 |
| 90 | 512 | 20811 | 111 | 2643 |
| 120 | 426 | 20811 | 82 | 2643 |

For example, Table 10 indicates that 426 NREM apnea segments and 20811 NREM normal segments trained LAMSTAR neural network 440 to make predictions of obstructive sleep apnea syndrome during NREM sleep 120 seconds in advance.

Figures 11A, 11B:
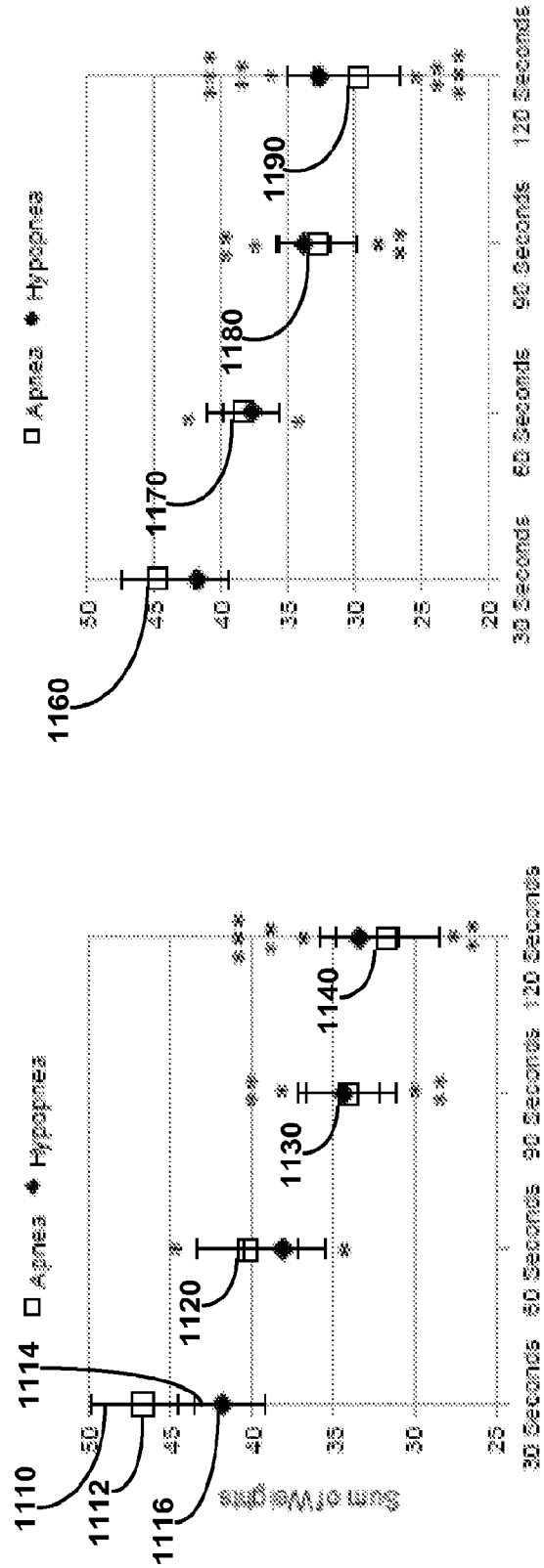
FIG. 11A is a graph of sums of LAMSTAR link-weights as a function of prediction lead time for true positive decisions.
FIG. 11B is a graph of sums of LAMSTAR link-weights as a function of prediction lead time for false negative decisions.

FIGS. 11A and 11B sums of link-weights leading from every winning SOM node of LAMSTAR neural network 440 to an output node of LAMSTAR neural network 440 as a function of lead time. FIG. 11A is a graph of sums of link-weights of LAMSTAR neural network 440 as a function of prediction lead time for true positive decisions; that is, decisions where LAMSTAR neural network 440 correctly predicted apnea or hypopnea. Similarly, FIG. 11B is a graph of sums of link-weights of LAMSTAR neural network 440 as a function of prediction lead time for false negative decisions; that is, decisions where LAMSTAR neural network 440 indicated breathing was normal, even though the patient had an episode of apnea or hypopnea. Both FIGS. 11A and 11B use open boxes to depict sums of link weights related to apnea and use filled diamonds to depict sums of link weights related to hypopnea.

As discussed above for FIGS. 4, 5A, and 5B, particular embodiments of LAMSTAR neural network 440 adjust link-weights in the link-weight matrix L between nodes in SOM layer(s) and the output layer by incrementing link weights during training for desired outputs and decrementing link weights during training for incorrect outputs. In these particular embodiments, sums of link weights of LAMSTAR neural network 440 during operation estimate an "event proximity" or duration of time in the future before an event will occur.

FIG. 11A indicates that sums for true positive decisions increase as lead time decreases. Similarly, FIG. 11B indicates that sums of link weights for false negative decisions increase as lead time decreases.

Since sums of link-weights increase the closer to an impending event, even for false negative events, the sum of link-weights provides an estimate of event proximity. Furthermore, T-tests of the sums of link-weights for true positive results shown in FIG. 11A indicates the results within FIG. 11A are nearly all statistically distinguishable over all lead times. That is, the lead times can be statistically differentiated from each other based on sums of link-weights. Similarly, T-tests indicate the sums of link-weights for false negative results as shown in FIG. 11B are nearly all statistically distinguishable over all lead times.

A duration of event proximity can be estimated by determining a sum of link-weights and comparing the sum of link-weights to one or more thresholds. For example, for true positive results, FIG. 11A shows sum of link weights for 30-second lead time apnea prediction 1112 is approximately 47, sum of link weights for apnea prediction for a 60-second lead time 1120 is approximately 40, sum of link weights for apnea prediction for a 90-second lead time 1130 is approximately 34, and sum of link weights for apnea prediction for a 30-second lead time 1140 is approximately 32. Similarly, FIG. 11B shows, for false negative results, sum of link weights for 30-second lead time apnea prediction 1160 is approximately 45, sum of link weights for apnea prediction for a 60-second lead time 1120 is approximately 38, sum of link weights for apnea prediction for a 90-second lead time 1130 is approximately 32, and sum of link weights for apnea prediction for a 30-second lead time 1140 is approximately 30.

Continuing this example, a sum of link weights greater than or equal to 41 indicates an apnea-event proximity of 30 seconds. Similarly, a sum of link weights greater than or equal to 33 indicates an apnea-event proximity within 60 seconds. In this example, a 30-second apnea-event-proximity threshold with a value of 41 is used, and a 60-second apnea-event-proximity threshold with a value of 35 is used.

In an example technique to determine an event proximity, a sum of link weights S is determined. In this example, an apnea-event proximity of 30 seconds is determined when S exceeds the 30-second apnea-event-proximity threshold. If S does not exceed the 30-second apnea-event-proximity threshold but does exceed the 60-second apnea-event-proximity threshold, an apnea-event proximity of 60 seconds is determined. If S is less than the 60-second apnea-event-proximity threshold, the event proximity would be undetermined at that time.

In other scenarios and examples, more or fewer event-proximity thresholds with different numerical data can be used. In still other scenarios and examples, event proximities for different events than the example of apnea events can be determined using the technique mentioned above of determining sums of link weights and comparing those sums to thresholds.

In some embodiments, event proximities equal or exceed segment sizes. For example, if 30-second long segments were used by LAMSTAR neural network 440 to generate a prediction of sleep apnea syndrome with an apnea-event proximity of 90 seconds, the apnea-event proximity would exceed the 30-second segment duration.

Apnea and Hypopnea Detection

Figure 12A:
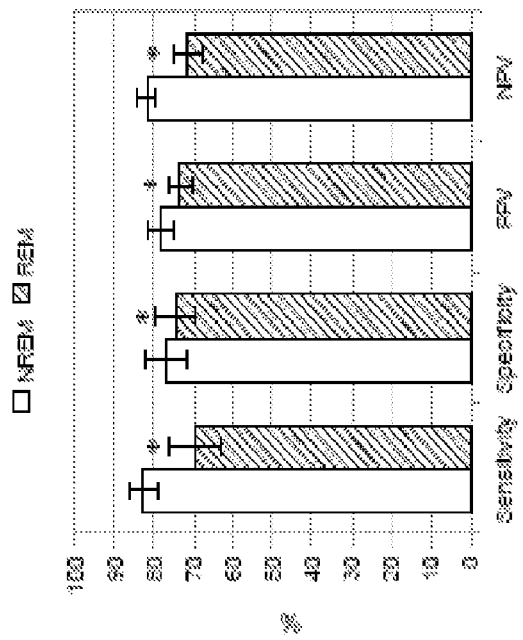
FIG. 12A shows results of detection of sleep apnea syndrome events during both NREM sleep and REM sleep.

FIG. 12A shows results of detection of sleep apnea syndrome events during both NREM sleep and REM sleep. Sleep apnea detection was tested during 30-second segments only, based on experience with sleep apnea prediction. For REM apnea detection, the sensitivity was 82.7±1.9%, the specificity was 86.1±1.3%, the PPV was 85.6±1.0%, and the NPV was 83.3±1.4%. For NREM apnea detection, the sensitivity was 88.6±1.2%, the specificity was 85.3±1.2%, the PPV was 85.8±0.9%, and the NPV was 88.3±1.0%.

Figure 12B:
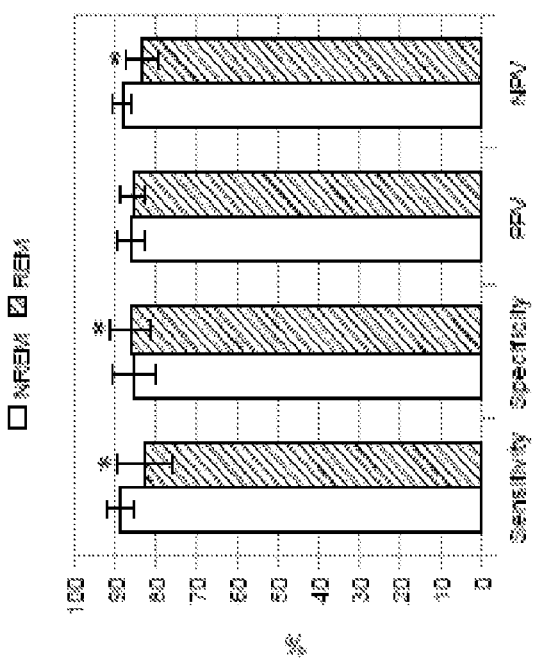
FIG. 12B shows results of detection of hypopnea events during both NREM sleep and REM sleep.

FIG. 12B shows results of detection of hypopnea events during both NREM sleep and REM sleep. As with sleep apnea events, hypopnea detection was tested during 30-second segments only, based on hypopnea prediction experiences. NREM hypopnea detection had a sensitivity of 82.8±3.5%, a specificity of 77.2±5.2%, a PPV of 78.6±3.3%, and a NPV of 81.9±2.4%. REM hypopnea detection had a sensitivity of 69.8±6.7%, a specificity of 74.5±5.0%, a PPV of 73.5±2.9%, and a NPV of 71.5±3.8%.

The most significant signals for apnea and hypopnea detection differed from apnea and hypopnea prediction. For apnea detection, the most important signal was oronasal temperature. For hypopnea detection, the most important signal was nasal pressure.

An Exemplary Method for Generating Physiological Event Results

Figure 13:
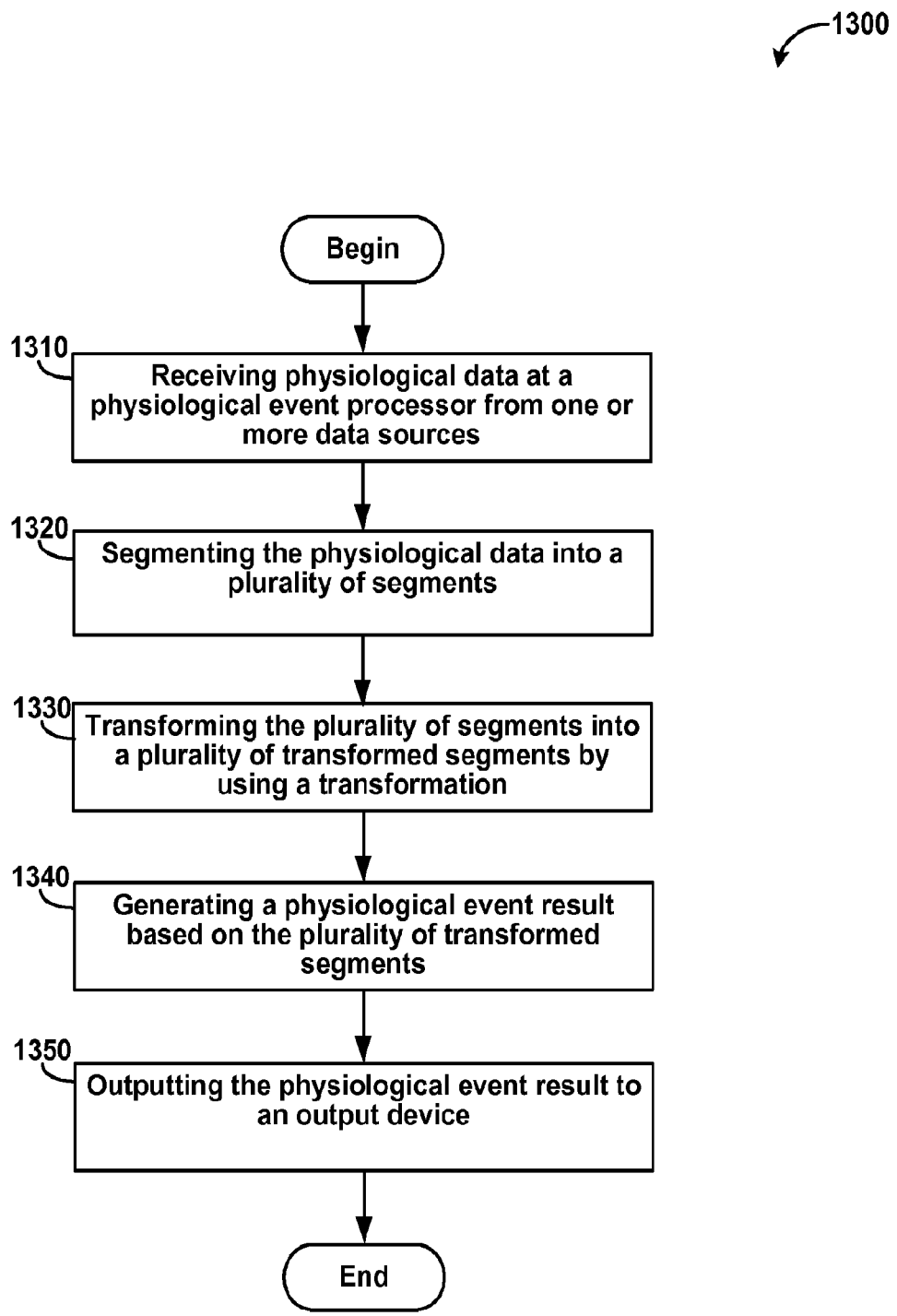
FIG. 13 is a flowchart depicting exemplary functional blocks of an exemplary method for generating physiological event results.

FIG. 13 is a flowchart depicting exemplary functional blocks of an exemplary method 1300 for generating physiological event results.

Initially, as shown at block 1310, physiological data are received at a physiological event processor from one or more input data sources. In some embodiments, the physiological event processor is a computing device, such as described above with respect to FIG. 3, and includes the functionality of a physiological event processor as described with respect to FIGS. 1, 2A, and 2B and/or the functionality of the data preprocessor and LAMSTAR neural network described above with respect to FIGS. 4, 5A, and 5B. In some scenarios, the physiological data are related to a patient. The physiological data are gathered from one or more input data sources.

As shown at block 1320, the physiological data are segmented at the physiological event processor into a plurality of segments. In some embodiments, each segment represents a predetermined duration of physiological data. The physiological data in each given segment of the plurality of segments are gathered from an input data source of the one or more input data sources. In some embodiments, the given segment includes an identification of an input data source for the given segment. Example segmentations of data are discussed above with respect to FIGS. 2A and 4.

As shown at block 1330, a plurality of segments are transformed into a plurality of transformed segments by using a transformation at the physiological event processor. In some embodiments, the plurality of segments are transformed using at least one transformation on the plurality of segments. Examples of generating segments and transformations are discussed above with respect to FIGS. 2A, 4, and 6A-6B.

As shown at block 1340, a physiological event result is generated at the physiological event processor based on the plurality of transformed segments. In some embodiments, the physiological event result includes information related to a physiological event. In particular embodiments, the physiological event result comprises a significance value of a significant input data source of the one or more input data sources. Significance values are discussed above in more detail with respect to FIG. 1. In other embodiments, physiological event result comprises an event proximity. Event proximities are discussed above in more detail with respect to FIGS. 11A and 11B.

Example physiological event results, such as predictions of physiological events and detection of physiological events, are discussed above with respect to FIGS. 1, 2B, 4, 5A, and 5B. A specific example of generating physiological event results for sleep-related physiological events is discussed above with respect to FIGS. 6A through 12B, inclusive.

As shown at block 1350, the physiological event result is output from the physiological event processor to an output device. Example outputs are discussed above with respect to FIGS. 1, 2B, 4, 5A, and 5B.

Thus, physiological event results are generated and subsequently output. The output physiological event results are suitable for use in patient diagnosis, treatment (including but not limited to the control of medical devices), therapy, and/or monitoring.

It should be understood that the programs, processes, methods and systems described herein are not related or limited to any particular type of computer or network system (hardware or software), unless indicated otherwise. Various types of general purpose or specialized computer systems can be used with or perform operations in accordance with the teachings described herein.

It should be further understood that this and other arrangements described herein are for purposes of example only. As such, those skilled in the art will appreciate that other arrangements and other elements (e.g., machines, interfaces, functions, orders, and groupings of functions, etc.) can be used instead, and some elements can be omitted altogether according to the desired results. Further, many of the elements that are described are functional entities that can be implemented as discrete or distributed components or in conjunction with other components, in any suitable combination and location.

In view of the wide variety of embodiments to which the principles of the present application can be applied, it should be understood that the illustrated embodiments are examples only, and should not be taken as limiting the scope of the present application. For example, the steps of the flow diagrams can be taken in sequences other than those described, and more or fewer elements can be used in the block diagrams. While various elements of embodiments have been described as being implemented in software, in other embodiments hardware or firmware implementations can alternatively be used, and vice-versa.

The claims should not be read as limited to the described order or elements unless stated to that effect. Therefore, all embodiments that come within the scope and spirit of the following claims and equivalents thereto are claimed.

What is claimed is:

1. A method, comprising:
receiving, at a physiological event processor, physiological data related to a patient, the physiological data received from one or more input data sources;
segmenting, at the physiological event processor, the physiological data into a plurality of segments, wherein one or more segments of the plurality of segments represent a predetermined duration of physiological data gathered from an input data source of the one or more input data sources;
transforming, at the physiological event processor, the plurality of segments into a plurality of transformed segments by using at least one transformation on the plurality of segments;
determining a value of a statistic for each transformed segment in the plurality of transformed segments;
determining a histogram of the plurality of values of the statistic, wherein the histogram comprises a plurality of subsegments;
for each value of the plurality of values of the statistic:
determining a subsegment of the histogram associated with the value and
determining a code value for the associated subsegment of the histogram;
generating, at the physiological event processor, a physiological event result based on the plurality of code values, wherein the physiological event result comprises information related to a physiological event, and wherein the physiological event result further comprises a significance value of a significant input data source of the one or more input data sources; and
outputting the physiological event result from the physiological event processor to an output device.

2. The method of claim 1, wherein generating the physiological event result comprises generating the physiological event result using a system selected from the group consisting of a neural network, a digital signal processor, and/or an expert system.

3. The method of claim 1, wherein the physiological event processor comprises a neural network.

4. The method of claim 3, wherein the physiological event processor comprises a LArge Memory STorage And Retrieval (LAMSTAR) neural network.

5. The method of claim 1, wherein the code value is associated with a boundary of a subsegment of the histogram.

6. The method of claim 1, wherein the at least one transformation comprises a wavelet transformation.

7. The method of claim 1, wherein generating, at the physiological event processor, the physiological event result comprises predicting or detecting, at the physiological event processor, an occurrence of the physiological event.

8. The method of claim 7, wherein the physiological event processor comprises a neural network, and wherein predicting or detecting, at the physiological event processor, the occurrence of the physiological event comprises predicting the occurrence of the physiological event using the neural network.

9. The method of claim 8, wherein the neural network comprises a LAMSTAR neural network, and wherein predicting the occurrence of the physiological event using the neural network comprises generating a prediction of the occurrence of the physiological event using the LAMSTAR neural network.

10. The method of claim 9, wherein generating the prediction of the occurrence of the physiological event using the LAMSTAR neural network comprises determining the significance of the significant input data source via the LAMSTAR neural network.

11. The method of claim 9, wherein the prediction of the occurrence of the physiological event is an output decision of the LAMSTAR neural network.

12. The method of claim 1, wherein the physiological event processor comprises a data preprocessor, the data preprocessor comprising a digital signal processor, and wherein generating the plurality of transformed segments by using at least one transformation on the plurality of segments comprises generating the plurality of transformed segments using the data preprocessor.

13. The method of claim 12, wherein the data preprocessor comprises a wavelet transformer.

14. The method of claim 12, wherein transforming the plurality of segments into the plurality of transformed segments comprises generating parameters of individual frequency bands of a wavelet transform using the wavelet transformer.

15. The method of claim 1, wherein generating the physiological event result comprises detecting an occurrence of the physiological event.

16. The method of claim 1, wherein outputting the physiological event result comprises displaying the physiological event result.

17. The method of claim 1, wherein outputting the physiological event result comprises sending a command to an output device, the command based on the physiological event result.

18. An apparatus, comprising:
a processing unit;
a source data interface, configured to communicate with one or more input data sources;
an output interface;
data storage; and
machine-language instructions, stored in the data storage, that upon execution by the processing unit cause the processing unit to perform functions comprising:
receiving physiological data related to a patient via the source data interface,
segmenting the data into a plurality of segments, wherein one or more segments of the plurality of segments represent a predetermined duration of physiological data gathered from an input data source of the one or more input data sources,
transforming the plurality of segments into a plurality of transformed segments by using at least one transformation on the plurality of segments,
determining a value of a statistic for each transformed segment in the plurality of transformed segments,
determining a histogram based on the plurality of values of the statistic, wherein the histogram comprises a plurality of subsegments,
for each value of the plurality of the values of the statistic:
determining a subsegment of the histogram associated with the value and
determining a code value for the associated subsegment of the histogram,
generating a physiological event result based on the plurality of code values, wherein the physiological event result comprises a significance value of a significant input data source of the one or more input data sources, and
outputting the physiological event result via the output interface.

19. The apparatus of claim 18, wherein the physiological event result comprises an event proximity comprising an event-proximity duration, wherein the event-proximity duration is greater than or equal to the predetermined duration.

20. The apparatus of claim 19, wherein the event-proximity duration is a multiple of 30 seconds.

21. The apparatus of claim 19, wherein the physiological data are associated with a physiological condition related to sleep of the patient.

22. The apparatus of claim 21, wherein the physiological condition is a sleep apnea syndrome.

23. The apparatus of claim 22, wherein the physiological event result comprises a prediction of a sleep-apnea-syndrome event.

24. The apparatus of claim 22, wherein the physiological event result comprises a detection of a sleep-apnea-syndrome event.

25. The apparatus of claim 22, wherein the physiological event result comprises a prediction of a hypopnea event.

26. The apparatus of claim 22, wherein the physiological event result comprises a detection of a hypopnea event.

27. The apparatus of claim 18, wherein the at least one transformation is a wavelet transformation.

28. The apparatus of claim 18, further comprising a network-communication device, wherein receiving physiological data related to a patient further comprises receiving the physiological data via the network-communication device.

29. A non-transitory tangible computer-readable medium having instructions stored thereon that, upon execution by a computing device, cause the computing device to perform functions comprising:
receiving, at the computing device, physiological data related to a patient, the physiological data received from one or more input data sources;
segmenting, at the computing device, the data into a plurality of segments, wherein a segment of the plurality of segments represents a predetermined duration of physiological data gathered from an input data source of the one or more input data sources;
transforming, at the computing device, the plurality of segments into a plurality of transformed segments by using at least one transformation on the plurality of segments;
determining, at the computing device, a value of a statistic for each transformed segment in the plurality of transformed segments;
determining a histogram of the plurality of values of the statistic using the computing device, wherein the histogram comprises a plurality of subsegments;

for each value of the plurality of the values of the statistic, the computing device:
- determining a subsegment of the histogram associated with the value and
- determining a code value for the associated subsegment of the histogram;

generating, at the computing device, a physiological event result based on the plurality of code values, wherein the physiological event result comprises information related to a physiological event, and wherein the physiological event result further comprises a significance value of a significant input data source of the one or more input data sources; and outputting the physiological event result from the computing device.

* * * * *